(12) United States Patent
Back et al.

(10) Patent No.: US 11,234,862 B2
(45) Date of Patent: Feb. 1, 2022

(54) OPHTHALMIC LENSES AND METHODS FOR CORRECTING, SLOWING, REDUCING, AND/OR CONTROLLING THE PROGRESSION OF MYOPIA IN CONJUNCTION WITH USE OF ATROPINE OR RELATED COMPOUNDS

(71) Applicant: Brien Holden Vision Institute Limited, Sydney (AU)

(72) Inventors: Arthur Back, Danville, CA (US); Padmaja Rajagopal Sankaridurg, Maroubra (AU); Cathleen Fedtke, Casula (AU)

(73) Assignee: BRIEN HOLDEN VISION INSTITUTE LIMITED, Sydney (AU)

( * ) Notice: Subject to any disclaimer, the term of this patent is extended or adjusted under 35 U.S.C. 154(b) by 0 days.

(21) Appl. No.: 17/197,858

(22) Filed: Mar. 10, 2021

(65) Prior Publication Data
US 2021/0282966 A1   Sep. 16, 2021

Related U.S. Application Data

(60) Provisional application No. 63/010,235, filed on Apr. 15, 2020, provisional application No. 62/988,225, filed on Mar. 11, 2020.

(51) Int. Cl.
*A61F 9/00* (2006.01)
*G02C 7/04* (2006.01)
(Continued)

(52) U.S. Cl.
CPC ............ *A61F 9/0017* (2013.01); *A61K 31/46* (2013.01); *G02C 7/021* (2013.01); *G02C 7/022* (2013.01); *G02C 7/04* (2013.01)

(58) Field of Classification Search
CPC ........ A61K 31/46; G02C 7/022; G02C 7/021; G02C 7/04-049
(Continued)

(56) References Cited

U.S. PATENT DOCUMENTS

2014/0036225 A1\* 2/2014 Chehab ............... A61P 27/02
                                                      351/159.02
2018/0095296 A1   4/2018 Lin et al.
(Continued)

OTHER PUBLICATIONS

International Search Report dated May 5, 2021 for PCT/IB2021/051998.

*Primary Examiner* — Travis S Fissel
(74) *Attorney, Agent, or Firm* — Jones Day

(57) ABSTRACT

An ophthalmic lens for treating myopia comprising: a base lens with a front surface, a back surface, and a first power profile selected to correct or substantially correct for a distance refractive error of the eye; one or more myopia control elements on at least one of the front and back surfaces of the lens; a first viewing region having a dimension selected based, at least in part, on a concentration of a pharmaceutical agent for use in conjunction with an ophthalmic lens, the first viewing region being configured to minimize, reduce and/or eliminate vision disturbances for distance vision; and a second viewing region comprising a power profile that is relatively more positive compared to the first viewing region; wherein at least one of the size of the second viewing region and the relatively more positive power of the second viewing region is selected based, at least in part, on the concentration of the pharmaceutical agent.

30 Claims, 20 Drawing Sheets

(51) Int. Cl.
*G02C 7/02* (2006.01)
*A61K 31/46* (2006.01)

(58) Field of Classification Search
USPC ............ 351/159.02, 159.04–159.06, 159.11,
351/159.16, 159.41–159.43, 159.68,
351/159.73
See application file for complete search history.

(56) References Cited

U.S. PATENT DOCUMENTS

| | | |
|---|---|---|
| 2018/0373059 A1 | 12/2018 | Lin et al. |
| 2019/0125662 A1 | 5/2019 | Doshi |
| 2019/0353929 A1 | 11/2019 | Lin et al. |
| 2020/0012123 A1 | 1/2020 | Newman |

* cited by examiner

Fig 12
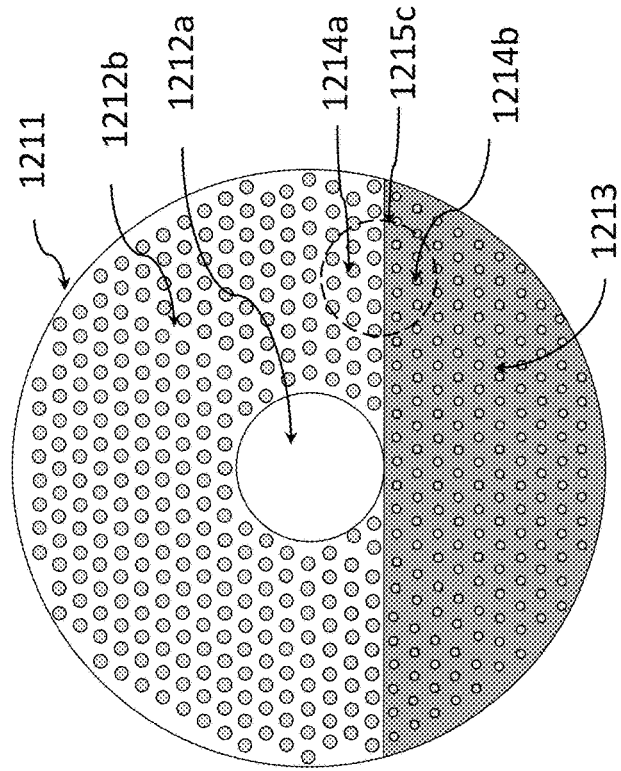
FIG. 12A
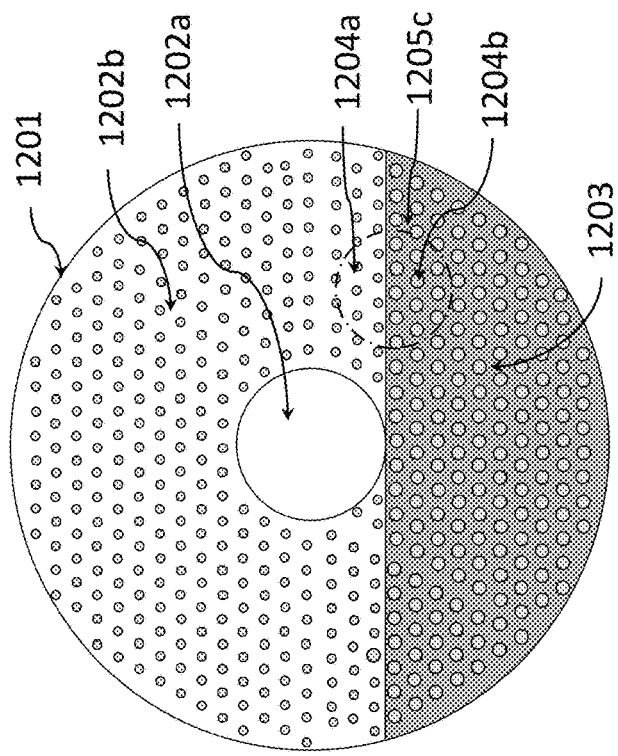
FIG. 12B
* $Fill\ Ratio\ (\%) = \frac{(Number\ of\ Myopia\ Control\ Elements) * Area\ of\ each\ Myopia\ Control\ Element)}{Area\ of\ Opthalmic\ Lens\ comprising\ Myopia\ Control\ Elements} * 100$
1205c: Fill Ratio in one of first viewing regions 1202b < Fill Ratio in the second viewing region 1203
1215c: Fill Ratio in the second viewing region 1213 < Fill Ratio in one of the first viewing regions 1212b Fig 13
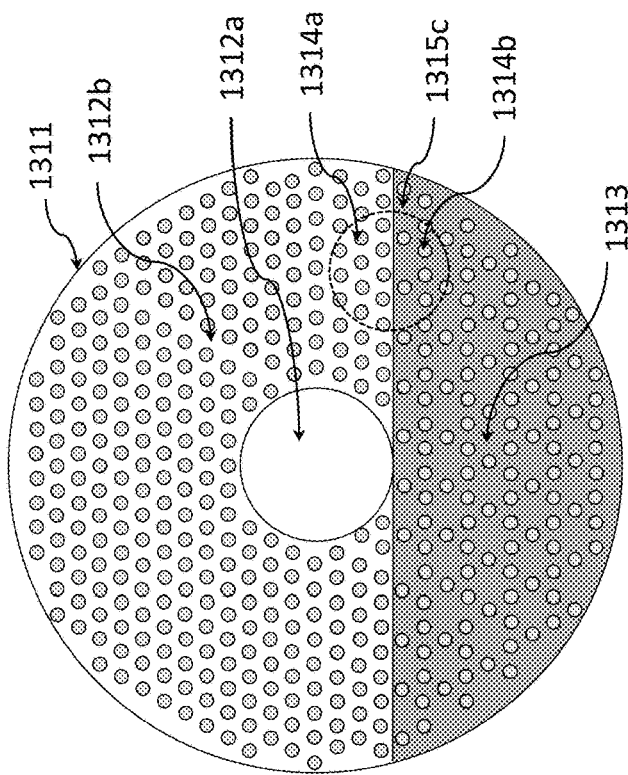
FIG. 13A
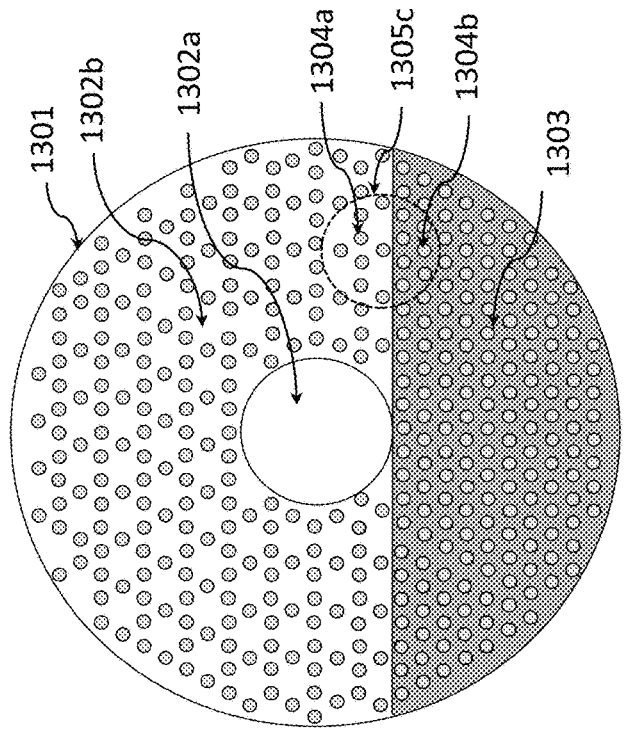
FIG. 13B
* Fill Ratio (%) = $\frac{(Number\ of\ Myopia\ Control\ Elements * Area\ of\ each\ Myopia\ Control\ Element)}{Area\ of\ Opthalmic\ Lens\ comprising\ Myopia\ Control\ Elements} * 100$
(1305c): Fill Ratio in one of the first viewing regions 1302b < Fill Ratio in the second viewing region 1303
(1315c): Fill Ratio in the second viewing region 1313 < Fill Ratio in one of the first viewing regions 1312b FIG. 17A Ophthalmic lens for use with low concentrations of Atropine FIG. 17B Ophthalmic lens for use with moderate to high concentrations of Atropine FIG. 17C Ophthalmic lens for use with high concentrations of Atropine

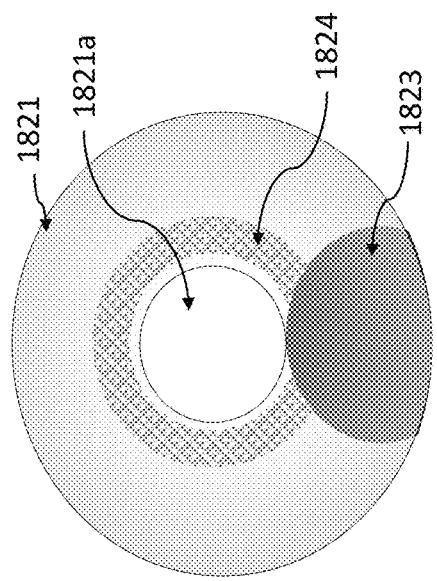
FIG. 18C Ophthalmic lens for use with high concentrations of Atropine
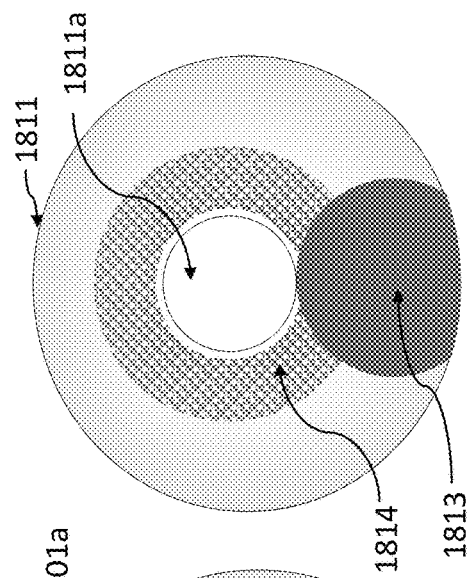
FIG. 18B Ophthalmic lens for use with moderate to high concentrations of Atropine
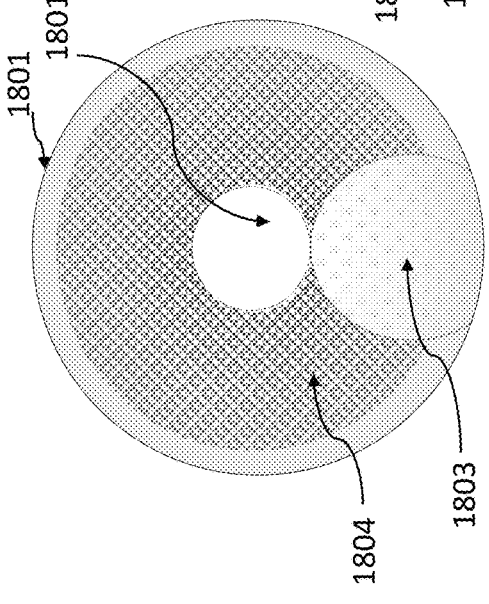
FIG. 18A Ophthalmic lens for use with low concentrations of Atropine
Fig 18

Fig 19C

| Ophthalmic lens selected for a myope prescribed 0.05% atropine and with symptoms of visual disturbance | Viewing region | Base power of refractive zone (D) | Myopia control element defocus power (ie additional power over refractive power of viewing zone) excluding central first viewing zones (D) | Myopia control element power (ie net power combined with base refractive power of viewing zone) (D) |
|---|---|---|---|---|
| EXAMPLE 1<br>Distance refractive error: -1.00<br>Reading addition: +2.00<br>Refractive Myopia control elements: +3.00D myopic defocus (1904, 1905). | First viewing regions (1902a, 1902b) | -1.00 | +3.00 (1904) | +2.00 (1904) |
| | Second viewing region (1903) | +1.00 | +3.00 (1905) | +4.00 (1905) |
| EXAMPLE 2<br>Distance refractive error: -5.00<br>Reading addition: +2.00<br>Refractive Myopia control elements: +3.00D myopic defocus (1904, 1905). | First viewing regions (1902a, 1902b) | -5.00 | +3.00 (1904) | -2.00 (1904) |
| | Second viewing region (1903) | -3.00 | +3.00 (1905) | 0.00 (1905) |
| EXAMPLE 3<br>Distance refractive error: -5.00D<br>Reading addition: +2.00D<br>Refractive Myopia control elements: -3.00D hyperopic defocus (1904, 1905). | First viewing regions (1902a, 1902b) | -5.00 | -3.00 (1904) | -8.00 (1804) |
| | Second viewing region (1903) | -3.00 | -3.00 (1905) | -6.00 (1905) |
| EXAMPLE 4<br>Distance refractive error: -1.00DS/-1.00DC x180<br>Reading addition: +2.00D<br>Refractive Myopia control elements: +2.00D myopic defocus (1904, 1905). | First viewing regions (1902a, 1902b) | -1.00/-1.00x180 | +1.00 (1904) | 0.00/-1.00x180 (1904) |
| | Second viewing region (1903) | +1.00/-1.00x180 | +2.00 (1905) | +3.00/-1.00x180 (1905) |
| EXAMPLE 5<br>Distance refractive error: -2.00D<br>Refractive Myopia control elements: +1.50D myopic defocus (1914) and +3.50D myopic defocus (1915). | First viewing regions (1912a, 1912b) | -2.00 | +1.50 (1914) | -0.50 (1914) |
| | First viewing region (1912c) | -2.00 | +3.50 (1915) | +1.50 (1915) |

OPHTHALMIC LENSES AND METHODS FOR CORRECTING, SLOWING, REDUCING, AND/OR CONTROLLING THE PROGRESSION OF MYOPIA IN CONJUNCTION WITH USE OF ATROPINE OR RELATED COMPOUNDS

CROSS-REFERENCE TO RELATED APPLICATIONS

This application claims priority to U.S. Provisional Application No. 62/988,225 entitled, Ophthalmic Lenses and Methods for Correcting, Slowing, Reducing, and/or Controlling the Progression of Myopia in Conjunction with Atropine or Related Compounds, filed on Mar. 11, 2020, and U.S. Provisional Application No. 63/010,235 entitled, Ophthalmic Lenses and Methods for Correcting, Slowing, Reducing, and/or Controlling the Progression of Myopia in Conjunction with Use of Atropine or Related Compounds, filed on Apr. 15, 2020. This application is related to International Application No. PCT/AU2018/051187 entitled, Pharmaceutical Compositions for Controlling and/or Reducing the Progression of Myopia, filed on Nov. 2, 2018, International Application No. PCT/AU2017/051173, entitled, Devices, Systems, and Methods for Myopia Control, filed on Oct. 25, 2017, U.S. Provisional Application No. 62/896,920 entitled, Ophthalmic Lenses and Methods for Correcting, Slowing, Reducing, and/or Controlling the Progression of Myopia, filed on Sep. 6, 2019, and U.S. Provisional Application No. 62/868,348 entitled, Ophthalmic Lenses and Methods for Correcting, Slowing, Reducing, and/or Controlling the Progression of Myopia, filed on Jun. 28, 2019. Each of these priority applications and related applications are incorporated herein by reference in their entirety.

TECHNICAL FIELD

This disclosure relates to ophthalmic lenses, and more particularly to designs and/or configurations for ophthalmic lenses, kits and/or series of ophthalmic lenses, and/or methods for correcting, slowing, reducing, and/or controlling the progression of myopia configured for use in conjunction with muscarinic receptor antagonists and/or related compounds.

BACKGROUND

The discussion of the background in this disclosure is included to explain the context of the disclosed embodiments. This is not to be taken as an admission that the material referred to was published, known or part of the common general knowledge at the priority date of the embodiments and claims presented in this disclosure.

Myopia, commonly referred to as shortsightedness, is a disorder of the eye that results in distant objects being focused in front of the retina. Accordingly, the image on the retina is not in focus and results in blurred vision. Optical correction strategies for myopia use ophthalmic lenses to shift the image plane to the retina and thereby provide clear vision. However, these strategies may not slow eye growth and therefore, myopia continues to progress. Used topically, Atropine, a muscarinic receptor antagonist, has demonstrated a level of efficacy in slowing myopia progression. Other myopia control strategies include progressive addition lenses, executive bifocal spectacles, dual focus contact lenses, spectacles with multiple segments, spectacle lenses with scattering features, and orthokeratology.

Although the mechanism of action is still unknown, varying concentrations of Atropine eye drops (0.01% to 1.0%) have been used and there is a concentration dependent response e.g., the higher the concentration, the greater the efficacy. However, the increased side-effects associated with higher doses of Atropine including near blur, photophobia and risk of ultraviolet exposure leading to potential crystalline lens and retinal changes often deter parents and/or caretakers from widely adopting higher concentrations for treatment in the young and therefore limits efficacy. Furthermore, although Atropine may slow the progression of myopia, the efficacy may vary between individuals with some individuals receiving benefit and others not as much.

In addition, due to the loss of accommodative amplitude and resultant near blur induced by certain concentrations of Atropine, they require a concomitant use of an optical aid with near add (relatively more plus power compared to distance power) for near tasks. Another side-effect from Atropine use is photophobia. Research found that myopic children aged 8-10 years receiving atropine 0.5%, 0.1%, and 0.01% request photochromic progressive lenses 70%, 61%, and 6% of the time respectively.

Accordingly, there is a need to provide an ophthalmic lens that can be used in conjunction with a pharmaceutical agent, such as Atropine (or a muscarinic receptor antagonist, or a related compound more generally) that not only corrects the refractive error of the eye, but aids in further slowing the progression of myopia and/or reduces/minimizes visual disturbance(s). The embodiments described herein may solve or address one or more of these and/or other problems disclosed herein. The present disclosure is also directed to pointing out one or more advantages to using exemplary ophthalmic lenses and methods described herein.

SUMMARY

The present disclosure is directed, at least in part, to addressing, overcoming and/or ameliorating one or more of the problems described herein.

The present disclosure is directed, at least in part, to ophthalmic lenses, designs and configurations for ophthalmic lenses and/or methods or systems or series or kits which may be advantageously used in conjunction with one or more pharmaceutical agents to correct, slow, reduce, and/or arrest myopia.

In some embodiments, the pharmaceutical agent may be an agent that can slow, reduce and/or arrest myopia. In some embodiments, the pharmaceutical agent may be an agent that results in a change in one or more of the parameters of the eye including the pupillary diameter, accommodative changes, binocular vision disturbances, visual disturbances and/or any combination thereof. In some embodiments, the pharmaceutical agent may be an agent that results in pupil mydriasis. In some embodiments, the pharmaceutical agent may be an agent that results in accommodative dysfunction.

In some embodiments, the pharmaceutical agent may be a muscarinic receptor antagonist, including, for example, Atropine, pirenzepine, tropine, atropine sulfate, noratropine, atropine-N-oxide, tropine, tropic acid, atropine sulfate, diphenhydramine, dimenhydrinate, dicyclomine, flavoxate, oxybutynin, tiotropium, hyoscine, scopolamine (L-hyoscine), hydroxyzine, ipratropium, tropicamide, cyclopentolate, pirenzepine, homatropine, solifenacin, darifenacin, benzatropine, mebeverine, procyclidine, aclidinium bromide, trihexyphenidylbenzhexol, tolterodine, or a pharmaceutically acceptable salt thereof.

The present disclosure is directed, at least in part, to an ophthalmic lens that may be provided and/or may be used in conjunction with a muscarinic receptor antagonist (e.g., Atropine or Atropine based compounds) for slowing myopia. The ophthalmic lens may comprise a feature configured, at least in part, based on the concentration of the muscarinic receptor antagonist (e.g., Atropine or Atropine based compounds) in use. The ophthalmic lens may have features for correcting the refractive error of the eye and features to slow, reduce, and/or arrest the progression of myopia.

In some embodiments, an ophthalmic lens is provided and/or may be used in conjunction with a muscarinic receptor antagonist (e.g., Atropine or Atropine based compounds) for slowing the progression of myopia. The ophthalmic lens may comprise a feature configured, at least in part, based on the concentration of for example, Atropine or Atropine based compounds in use. The ophthalmic lens may have one or more features for correcting the refractive error of the eye, one or more features to slow, reduce, and/or arrest myopia, and/or one or more features to minimize or reduce visual disturbances at all (or substantially all) viewing distances.

In some embodiments, the ophthalmic lens to be used in conjunction with a muscarinic receptor antagonist (e.g., Atropine or Atropine related compounds) may comprise a base lens with a front and back surface. In some embodiments, the ophthalmic lens may further comprise one or more myopia control elements to slow myopia that may be incorporated in and/or on the base lens and/or interspersed or disposed across the lens. In some embodiments, the one or more myopia control elements may be disposed across the entire lens or may be disposed in one or more regions of the lens. In some embodiments, the one or more myopia control elements of the ophthalmic lens may be refractive, diffractive, contrast modulating, phase-modulating, meta-surfaces, light scattering, light-deviating, amplitude modulating, aberrated, holographic, light-diffusing elements, or a combination of one or more elements thereof. In some embodiments, the one or more myopia control elements may be discrete elements or may be continuous elements. In some embodiments, the one or more discrete myopia control elements may be positioned apart from the other myopia control elements. In some embodiments, the one or more discrete myopia control elements may be positioned in contact with or conjoined with or fused with one or more of other myopia control elements or a combination thereof. In some embodiments, the refractive elements may be shaped as a circular element, ring, arc, triangular, spiral or any other shape or a combination thereof or shaped as a continuous refractive power profile. In some embodiments, the refractive elements may be designed to provide no defocus, hyperopic defocus, myopic defocus, extended depth of focus or a combination thereof compared to refractive power profile in one or more first viewing regions designed to correct for the distance refractive error of the eye. In some embodiments, the one or more myopia control elements may be present across one or both surfaces or in between the surfaces or incorporated into the bulk of the ophthalmic lenses and may be present across the entire surface or limited to one or more regions of the lens In some embodiments, an ophthalmic lens is provided and/or may be used in conjunction with a muscarinic receptor antagonist, for example, Atropine or Atropine based compounds for slowing the progression of myopia. The ophthalmic lens may have one or more myopia control elements to slow, reduce, and/or arrest myopia. In some embodiments, the ophthalmic lens has one or more first viewing regions that incorporate a power profile that substantially corrects for the distance refractive error of the eye. In some embodiments, at least one of the one or more first viewing regions has a feature that is selected at least in part, to minimize, reduce or eliminate visual disturbances for the user when used in conjunction with Atropine. In some embodiments, at least one of the one or more first viewing regions may be sized based, at least in part, on the concentration of the muscarinic receptor antagonist (e.g., Atropine or Atropine related compounds) in use. In some embodiments, at least one of the one or more first viewing regions may correct for one or more of higher order aberrations induced, at least in part, by an increase in pupillary diameter. The ophthalmic lens may have one or more first viewing regions that incorporate a power profile that substantially corrects for the distance refractive error of the eye and at least one of the first viewing regions has one or more features selected to minimize or reduce visual disturbances at all (or substantially all) viewing distances and is based at least in part on the concentration of Atropine or Atropine related compounds.

In some embodiments, an ophthalmic lens is provided and/or may be used in conjunction with Atropine or Atropine based compounds for slowing the progression of myopia. The ophthalmic lens may have one or more myopia control elements to slow, reduce, and/or arrest myopia. The ophthalmic lens may have one or more first viewing regions that corrects for the distance refractive error of the eye and at least one of the first viewing regions has one or more features selected to minimize or reduce visual disturbances at all (or substantially all) viewing distances and is selected based at least in part on the concentration of Atropine or Atropine related compounds. In some embodiments, the ophthalmic lens may have one or more second viewing regions designed to provide acceptable vision for intermediate and/or near viewing distances and/or positioned elsewhere on the ophthalmic lens relative to at least one of one or more of the first viewing regions (e.g., the one or more of the first viewing regions selected to minimize or reduce visual disturbances). In some embodiments, the one or more second viewing regions having one or more features selected to provide acceptable vision for intermediate and/or near viewing distances may incorporate a power profile that is relatively more positive compared to the power profile of one or more first viewing regions. The relatively more positive power (or add power) of one of the second viewing regions is based at least in part on the concentration of Atropine or Atropine related compounds and designed to provide acceptable vision for intermediate and/or near distances. In some embodiments, the size and/or the relatively more positive power of the second viewing region may be selected based, at least in part, on the concentration of Atropine or Atropine related compounds in use. In some embodiments, the ophthalmic lens may have one or more second viewing regions designed to provide acceptable vision for intermediate and/or near viewing distances and selected to minimize or reduce visual disturbances. In some embodiments, at least one of the one or more second viewing regions may correct for one or more of higher order aberrations induced, at least in part, by an increase in pupillary diameter. In some embodiments, the type, size, arrangement, position, power profile, fill factor of one or more myopia control elements in one or more of the second viewing regions may be selected based, at least in part, on the concentration of pharmaceutical agent in use to minimize or reduce visual disturbances. In some embodiments, the one or more second viewing regions may be positioned at any combination of one or more of inferior, superior, temporal, nasal, oblique, concentric co-axial, concentric non co-axial, eccentric, non-concentric, inferonasal, inferotemporal, or any other position or combination thereof relative to at least one of the one or more first viewing regions.

In some embodiments, the ophthalmic lens has a second viewing region positioned inferiorly relative to the first viewing region for distance and has a power profile that is relatively more positive than the power profile of the first viewing region that is based at least in part on the concentration of concentration of Atropine or Atropine related compounds in use and provides acceptable vision for near distances. In some embodiments, the relatively more positive power profile of one or more second viewing regions may be relatively uniform or may be relatively non-uniform across the viewing region. In some embodiments, the relatively more positive power profile of the one or more second viewing regions may be progressive across the viewing region with the least amount of relatively more positive power positioned at the boundary between the first viewing region and the second viewing region and the most amount of relatively more positive power positioned towards the periphery further away from the boundary between the first viewing region and the second viewing region.

In some embodiments, the ophthalmic lens may further comprise one or more of a light absorbing filter or a light absorbing element or a photochromic filter or a photomask or a phase-shift mask to further reduce, minimize or eliminate visual disturbance for the eye. In some embodiments, the ophthalmic lens may further comprise a light absorbing filter or a photo mask or a phase shift mask in one or more first viewing regions and/or second viewing regions. In some embodiments, the ophthalmic lens may further comprise a light absorbing filter and/or an element that may range in density across one or more of the viewing regions. In some embodiments, the color and/or intensity of the light absorbing element, light absorbing filter or a photochromic filter may be based, at least in part, on the concentration of the muscarinic receptor antagonist (e.g., Atropine or Atropine related compounds) in use. In some embodiments, the color/wavelength of light absorption and/or intensity of the light absorbing element, or a photochromic filter may be based, at least in part, on the concentration of the muscarinic receptor antagonist (e.g., Atropine or Atropine related compounds) and the color of the iris of the eye.

The present disclosure is directed, at least in part, to a method for improving the rate for slowing of myopia. The method comprises providing an ophthalmic lens in conjunction with a muscarinic receptor antagonist (e.g., Atropine or Atropine related compounds) for use in an eye with myopia. In some embodiments, the ophthalmic lens may comprise one or more myopia control elements to slow the progression of myopia. In some embodiments, the one or more myopia control elements may be disposed across the entire lens or may be disposed in one or more regions of the lens. The ophthalmic lens may have one or more first viewing regions that substantially corrects for the distance refractive error of the eye and at least one of the first viewing regions has one or more features selected to minimize or reduce visual disturbances at all (or substantially all) viewing distances and based at least in part on the concentration of Atropine or Atropine related compounds. In some embodiments, the ophthalmic lens may further comprise one or more second viewing regions, positioned on the ophthalmic lens relative to the first second viewing regions and may incorporate a power profile that is relatively more positive compared to the power profile of one or more first viewing regions (e.g., the at least one of the first viewing regions having one or more features selected to minimize or reduce visual disturbances). The relatively more positive power (or add power) of one of the second viewing regions is based at least in part on the concentration of Atropine or Atropine related compounds and designed to provide acceptable vision for intermediate and/or near distances. In some embodiments, the one or more second viewing regions may be positioned inferior, superior, temporal, nasal, oblique, concentric co-axial, concentric non co-axial, eccentric, non-concentric, inferonasal, inferotemporal, or any other position or combination of one or more thereof. In some embodiments, the ophthalmic lens may further comprise a light absorbing filter or a light absorbing element or a photochromic filter or a photo mask or a phase shift mask to reduce, minimize and/or eliminate visual disturbance for the eye. In some embodiments, the light absorbing filter or the light absorbing element or the photochromic filter or the photo mask or the phase shift mask may be present in one or more of the first and/or second viewing regions and based at least in part on the concentration of Atropine or Atropine related compounds. In some embodiments, the color, wavelength of absorption, location/distribution and/or intensity of the light absorbing element, or a photochromic filter may be selected based, at least in part, on the muscarinic receptor antagonist (e.g., concentration of Atropine or Atropine related compounds) in use. In some embodiments, the pitch structure, depth, type, intensity and absorber of the photo mask and/or phase shift mask may be selected based, at last in part, on the muscarinic receptor antagonist in use.

The present disclosure is directed, at least in part, to a kit or set or series of ophthalmic lenses to be used in conjunction with a muscarinic receptor antagonist (e.g., Atropine or Atropine related compounds) for slowing the progression of myopia. The kit comprises a plurality of ophthalmic lenses that comprise one or more features configured or selected to be used based on the concentration of the muscarinic receptor antagonist (e.g., Atropine or Atropine related compounds). The one or more ophthalmic lenses in the kit or set or series comprises a base lens with a front and back surface. In some embodiments, the ophthalmic lens in the kit or set or series may comprise one or more myopia control elements to slow myopia. In some embodiments, the one or more myopia control elements of the ophthalmic lens may be refractive, diffractive, contrast modulating, phase-modulating, meta-surfaces, light scattering, light-deviating, amplitude modulating, aberrated, holographic, light-diffusing elements, or a combination of one or more elements thereof. The ophthalmic lens may have one or more first viewing regions that substantially corrects for the distance refractive error of the eye and at least one of the first viewing regions has one or more features selected to minimize or reduce visual disturbances at all (or substantially all) viewing distances and based at least in part on the concentration of Atropine or Atropine related compounds. In some embodiments, the kit or series comprises ophthalmic lenses with varying dimensions for at least one of one or more of the first viewing regions designed to minimize visual disturbances and are selected based, at least in part, on the concentration of the muscarinic receptor antagonist (e.g., Atropine or Atropine related compound) in use. In some embodiments, the size of the one or more of the first viewing regions designed to minimize visual disturbances may vary between the ophthalmic lenses in the series or set or kit and is selected to be used in conjunction with a particular concentration of atropine. In some embodiments, the one or more first viewing regions may control, reduce and/or minimize one or more of higher order aberrations to minimize visual disturbances and the aberration control may vary between the ophthalmic lenses in the series or set or kit. In some embodiments, the size and/or aberration control of the one or more of the first viewing regions may be designed to minimize visual disturbances and may vary between the ophthalmic lenses in the series or set or kit and is selected to be used in conjunction with a particular concentration of atropine In some embodiments, the size of the one or more first viewing regions designed to minimize visual disturbances for the eye may be relatively smaller in size when used in conjunction with lower concentrations of atropine compared to the size of the first viewing region used in conjunction with higher concentrations of atropine.

In some embodiments, the ophthalmic lenses in the set or kit or series may further comprise one or more second viewing regions, positioned on the ophthalmic lens relative to the first viewing regions and may incorporate a power profile that is relatively more positive compared to the power profile of one or more first viewing regions. The relatively more positive power (or add power) and/or size of one of the second viewing regions is based at least in part on the concentration of Atropine or Atropine related compounds and designed to provide acceptable vision for intermediate and/or near distances. In some embodiments, the one or more second viewing regions may be positioned inferior, superior, temporal, nasal, oblique, concentric co-axial, concentric non co-axial, eccentric, non-concentric, inferonasal, inferotemporal, or any other position or combination of one or more thereof on the ophthalmic lens relative to at least one of the one or more first viewing regions. In some embodiments, the kit comprises ophthalmic lenses with varying degrees of relatively more positive power profile in one or more second viewing regions that are selected for use based, at least in part, on the concentration of the muscarinic receptor antagonist (e.g., Atropine or Atropine related compound) in use. In some embodiments, the ophthalmic lens may further comprise a light absorbing filter or a light absorbing element or a photochromic filter or a photo mask or a phase shift mask or any other optical mask to further reduce, minimize or eliminate visual disturbance for the eye. In some embodiments, the light absorbing filter or the light absorbing element or the photochromic filter or the photo mask or the phase shift mask may be present in one or more of the first and/or second viewing regions and based at least in part on the concentration of Atropine or Atropine related compounds. In some embodiments, the color, wavelength of absorption, location/distribution and/or intensity of the light absorbing element or a photochromic filter may be selected based, at least in part, on the concentration of the muscarinic receptor antagonist (e.g., Atropine or Atropine related compound) in use. In some embodiments, the pitch structure, depth, type, intensity and absorber of the photo mask and/or phase shift mask may be selected based, at last in part, on the muscarinic receptor antagonist in use.

Some embodiments described herein may provide for a set or series of ophthalmic lenses to be used in conjunction with the muscarinic receptor antagonist (e.g., Atropine or Atropine related compound) for slowing myopia. The set or series of lens designs for ophthalmic lenses may comprise one or more lens designs with one or more features configured or selected to be used based, at least in part, on the concentration of the muscarinic receptor antagonist (e.g., Atropine or Atropine related compound) in use. The one or more ophthalmic lenses in the set or series comprises a base lens with a front and back surface. In some embodiments, the ophthalmic lens may comprise one or more myopia control elements may be disposed across the entire lens or may be disposed in one or more regions. The ophthalmic lens may have one or more first viewing regions that substantially corrects for the distance refractive error of the eye and at least one of the first viewing regions has one or more features selected to minimize or reduce visual disturbances at all (or substantially all) viewing distances and based at least in part on the concentration of Atropine or Atropine related compounds. In some embodiments, the size of the one or more first viewing regions designed to minimize or reduce visual disturbances for the eye may be relatively smaller in size when used in conjunction with lower concentrations of Atropine compared to the size of the first viewing region used in conjunction with higher concentrations of Atropine. In some embodiments, the one or more first viewing regions may further incorporate a power profile to control, minimize and/or reduce one or more of higher order aberrations to minimize visual disturbances and the type, magnitude of control or minimization of one or more of higher order aberrations may vary between the ophthalmic lenses depending on the concentration of Atropine. In some embodiments, the size of the one of one or more first viewing regions may be combined with a photo mask or a phase shift mask and/or controlled for aberrations to minimize or reduce visual disturbances for the eye and based at least in part of the concentration of Atropine or Atropine related compounds.

In some embodiments, the ophthalmic lens may further comprise one or more second viewing regions, positioned on the ophthalmic lens relative to at least one of the first viewing regions and may incorporate a power profile that is relatively more positive compared to the power profile of the at least one of the first viewing regions. The relatively more positive power (or add power) and/or size of one of the second viewing regions is based at least in part on the concentration of Atropine or Atropine related compounds and designed to provide acceptable vision for intermediate and/or near distances. In some embodiments, the location/position, strength/intensity, and the size of the myopia control elements across one or more of the first viewing regions and/or across one or more of the second viewing zones may be chosen to minimize or reduce visual disturbances to the eye and selected based at least in part on the concentration of Atropine or Atropine related compounds. In some embodiments, the relation between the type, location, strength, size, and the area occupied by one or more of the myopia control elements and the size of at least one of one or more first viewing regions may be designed to minimize or reduce visual disturbances to the eye and selected, based at least in part on the concentration of Atropine or Atropine related compounds. In some embodiments, when used in conjunction with lower concentrations of ≤0.01% atropine compared to >0.01% atropine, the size of at least one of the one or more first viewing regions that incorporates the distance refractive error and designed to minimize visual disturbances for the eye of the wearer may be relatively smaller in size whereas the strength and/or size and/or area occupied by one or more myopia control elements may be relatively higher.

In some embodiments, at least one of the one or more first viewing regions and one of one or more of the second viewing regions may be completely free or substantially free of the myopia control elements to reduce, minimize or eliminate visual disturbances for the user. In some embodiments, the one or more myopia control elements may be present in one of one or more first viewing regions and one of one or more of second viewing regions and the type, size, arrangement and fill factor of the myopia control elements may vary between the regions. In some embodiments, the arrangement, size, magnitude and/or strength of the one or more of myopia control elements comprising one or more of refractive, diffractive, prismatic, contrast modulating, phase-modulating, meta-surfaces, light scattering, light-deviating, amplitude modulating, aberrated, holographic, light-diffusing elements, or a combination of one or more elements thereof to be used in conjunction with the muscarinic receptor antagonist (e.g., Atropine or Atropine related compound) may be varied across the regions of the ophthalmic lens based on the rate of myopia progression of the eye.

In some embodiments, the ophthalmic lens to be used in conjunction with muscarinic receptor antagonist (e.g., Atropine or Atropine related compound) may comprise a light absorbing filter or a light absorbing element or a photochromic filter or a photo mask or a phase shift mask to further reduce, minimize and/or eliminate visual disturbance for the eye. In some embodiments, the ophthalmic lens to be used in conjunction with muscarinic receptor antagonist (e.g., Atropine or Atropine related compound) may comprise a prism or prism component across one or more of the first viewing regions and/or one of the second viewing regions to further reduce, minimize, and/or eliminate visual disturbance for the eye.

In some embodiments, the ophthalmic lens may be a spectacle lens comprising a feature configured based at least in part on a concentration of and for use in conjunction with one or more pharmaceutical agents for slowing the progression of myopia. In some embodiments, the ophthalmic lens may be a contact lens.

Other features and advantages of the subject matter described herein will be apparent from the description and drawings, and from the claims provided herein.

BRIEF DESCRIPTION OF THE DRAWINGS

Aspects of the embodiments described herein may be understood from the following detailed description when read with the accompanying figures.

FIGS. 4A to 4C illustrate the possible size/dimension of one of the first viewing regions of the ophthalmic lens to be used in conjunction with low, moderate, and high concentration of Atropine. FIG. 4D illustrates a non-circular first viewing region for an ophthalmic lens with myopia control features for use in conjunction with Atropine.

FIGS. 5A to 5C illustrate the possible size/dimension of one of the first viewing regions of the ophthalmic lens to be used in conjunction with low, moderate, and high concentration of Atropine.

FIGS. 7A to 7C illustrate the increasing magnitude of the relatively more positive power or more plus dioptric power in the second viewing regions relative to one of the first viewing regions and selected based on the strength of the concentration of Atropine prescribed for use.

FIGS. 8A to 8C illustrate the increasing area of the one of or more second viewing regions selected based on the strength of the concentration of Atropine prescribed for use.

FIGS. 10a to 10g illustrate the arrangement of the myopia control elements on the lens surface.

FIG. 12 is a schematic of an ophthalmic lens comprising one or more first viewing regions, one or more second viewing regions and one or more myopia control elements for use in conjunction with Atropine or other pharmaceutical agent for myopia. FIGS. 12A and 12B illustrate the variation in the fill ratio of the myopia control elements across the one or more second viewing regions and the one or more first viewing regions. The variation in fill ratio across the viewing regions is based on the size of the myopia control elements.

FIG. 13 is a schematic of an ophthalmic lens comprising one or more first viewing regions, one or more second viewing regions and one or more myopia control elements for use in conjunction with Atropine or other pharmaceutical agent for myopia. FIGS. 13A and 13B illustrate the variation in the fill ratio of the myopia control elements across the second viewing regions and the first viewing regions. The variation in fill ratio across the two regions is based on the distribution of the myopia control elements.

FIG. 14 illustrates the variation in the refractive power of the myopia control elements positioned from the upper edge of the ophthalmic lens to the lower edge of the ophthalmic lens.

FIG. 15 illustrates the variation in the fill ratio of the myopia control elements across the lens surface between FIGS. 15a and 15b. The fill ratio across the two regions is selected based on the concentration of Atropine for use and/or the rate of progression of myopia.

FIGS. 16A to 16C illustrate three ophthalmic lenses in the series 1601, 1611, and 1621 for use in conjunction with low, moderate and high concentration of atropine. The sizes of one of the one or more first viewing regions increase with increasing concentration of Atropine (1602a<1612a<1622a); the size and/or the relatively more positive power (Add power) of one of the second viewing regions increases in size with increasing concentrations of Atropine (1603<1613<1623).

FIGS. 17A to 17C illustrate three ophthalmic lenses in the series 1701, 1711 and 1721 designed for use in conjunction with low, moderate, and high concentration of atropine. The magnitude of the one or more myopia control elements decreases with increasing concentration of Atropine (1704>1714>1724);

FIG. 18 is a schematic of an ophthalmic lens series with the ophthalmic lenses comprising one or more first viewing regions, at least one second viewing regions and one or more myopia control elements and designed for use in conjunction with Atropine or other pharmaceutical agent for myopia. FIGS. 18A to 18C illustrate three ophthalmic lenses in the series 1801, 1811 and 1821 designed for use in conjunction with low, moderate, and high concentration of atropine. The area occupied by the one or more myopia control elements decreases with increasing concentrations of Atropine (1801>1811>1821). Additionally, the relatively more positive power in one of the second viewing regions increases with increasing concentration of Atropine (1823>1813>1803).

FIG. 19C illustrates an embodiment of the selection of the lens design based on the myopia history of an individual.

DETAILED DESCRIPTION

Figure 1B:
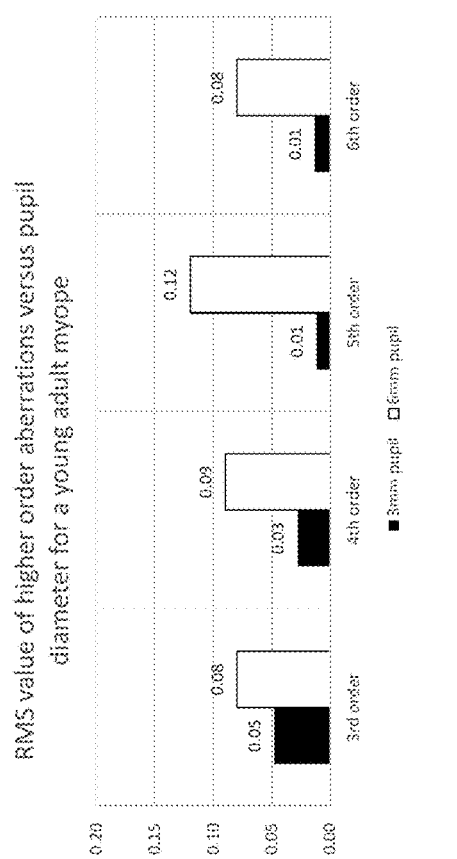
FIG. 1B demonstrates the increase in higher order aberrations ($3^{rd}$ to $6^{th}$ order) with an increase in pupil size (from 3 mm to 6 mm) for an emmetropic eye of a young adult.

The following disclosure provides many different embodiments, or examples, for implementing different features of the provided subject matter. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

The subject headings used in the detailed description are included for the ease of reference of the reader and should not be used to limit the subject matter found throughout the disclosure or the claims. The subject headings should not be used in construing the scope of the claims or the claim limitations.

The term "about" as used in this disclosure is to be understood to be interchangeable with the term approximate or approximately.

The term "comprise" and its derivatives (e.g., comprises, comprising) as used in this disclosure is to be taken to be inclusive of features to which it refers, and is not meant to exclude the presence of additional features unless otherwise stated or implied.

The term "myopia" or "myopic" as used in this disclosure is intended to refer to an eye that is already myopic, is pre myopic, or has a refractive condition that is progressing towards myopia.

The term "slow myopia" or "slow[ing] the progression of myopia" as used in this disclosure is intended to refer to attempts that either slow or reduce or minimize or arrest the rate of progression of myopia.

The term "ophthalmic lens" as used in this disclosure is intended to include any lens used for vision and may include a spectacle lens, a clip-on or stick-on feature on a spectacle lens, an electro-active spectacle lens, a contact lens, an intraocular lens or the like.

The term "pharmaceutical composition or agent" as used in this disclosure may be any agent, compound, chemical substance, formulation, a pharmaceutically acceptable salt, or combination thereof when delivered in whichever form or dosage results in a change in the pupillary diameter and/or accommodative changes and/or binocular vision disturbances and/or visual disturbances or a combination thereof. The pharmaceutical agent may refer to anticholinergics, particularly, muscarinic receptor antagonists such as atropine, atropine sulfate, noratropine, atropine-N-oxide, tropine, tropic acid, atropine methonitrate, diphenhydramine, dimenhydrinate, dicyclomine, flavoxate, oxybutynin, tiotropium, hyoscine, scopolamine (L-hyoscine), hydroxyzine, ipratropium, tropicamide, cyclopentolate, pirenzepine, homatropine, solifenacin, darifenacin, benzatropine, oxyphenonium, mebeverine, procyclidine, aclidinium bromide, trihexyphenidyl/benzhexol, tolterodine, a pharmaceutically acceptable salt thereof or atropine based compounds that include combination of atropine, atropine sulphate or products of atropine in combination with other compounds or other pharmaceutical compositions or agents.

The phrase "vision disturbance" as used in this disclosure is intended to refer to symptoms reported by individuals related to vision including glare, photophobia, double vision, haloes, flare, ghosting, shimmering, blurred vision, flickering vision, foggy vision, reduced contrast, aesthenopia or a combination thereof.

The phrase "accommodative dysfunction" as used in this disclosure is intended to refer to a reduction or a decrease or an imbalance or instability of the accommodative power or accommodative function or accommodative amplitude, or an imbalance between accommodation and convergence system that may result in one or more symptoms of vision disturbance and/or difficulties in viewing at near and intermediate distances.

The phrase "dimension" or "size" as used in this disclosure is intended to refer to one or more features of the ophthalmic lens relating to length, width, depth, shape, height, location or a combination of one or more features.

The phrase "in use" as used in this disclosure is intended to refer to the scenario where the treatment or agent or lens or system or kit is already in use or in use by the user and/or prescribed to be used and/or intended to be used.

Figure 1A:
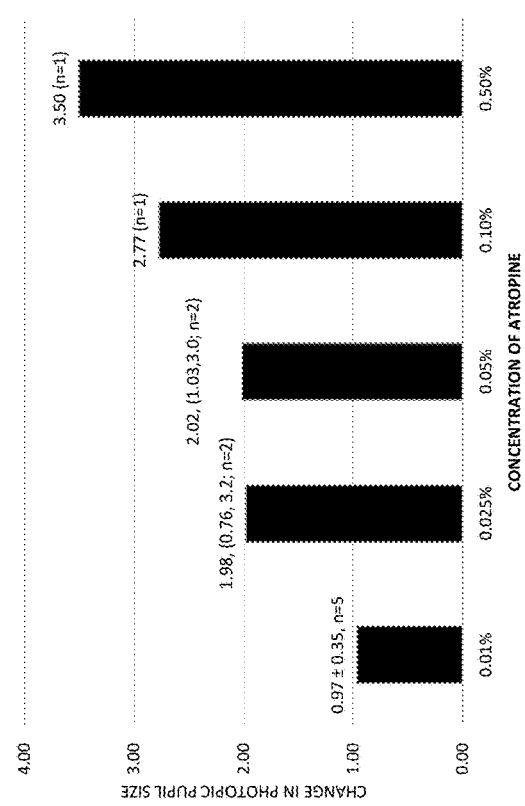
FIG. 1A illustrates the change in pupil size with Atropine concentrations ranging from 0.01% to 0.50%.

FIG. 1A illustrates a schematic plot of pupil diameters resulting from use of Atropine, a widely used muscarinic receptor antagonist and a pharmaceutical agent for myopia therapy. The average pupil diameter as a function of use of Atropine therapy is provided and shows an increase in photopic pupillary diameter with increasing concentration of Atropine. Considering FIG. 1A, it is observed that use of 0.01% Atropine which to date is the lowest concentration used for treatment of myopia in individuals, increases the photopic pupillary diameter by approximately 1 mm. Increasing the concentration to anywhere from 0.025% to 0.1% Atropine, increases the photopic pupil size from about 2 mm to about 3 mm. With the highest concentration of 0.5% Atropine, the increase in photopic pupil size was largest and at about 3 mm. An increase in pupil size increases aberrations of the eye. Although all types of aberrations increased significantly with increasing pupil size, an increase in certain higher order aberrations such as spherical aberrations may be more pronounced. FIG. 1B illustrates the increase in higher order aberrations from $3^{rd}$ to $6^{th}$ order as determined by aberrometry for the myopic eye of an individual who has a distance refractive error of approximately −2.00D. It is observed that there is a significant increase in aberrations with a larger pupil. An increase in the pupil size may result in a functional decrement in visual performance and one or more unwanted effects such as poorer visual performance, reduced contrast, blurred vision, increased glare and increased photophobia (sensitivity to light). In addition, use of muscarinic receptors antagonists in myopic individuals may also result in reduced or blurred vision at near distances due to reduction in the accommodative amplitude and/or may alter binocular vision status or may result in accommodative dysfunction. To reduce or lower the risk of the aforementioned side-effects associated with muscarinic antagonist therapy, it may be desirable to use lower concentrations of a pharmaceutical agent (e.g., Atropine). However, lower concentrations may not provide sufficient myopia control efficacy. Additionally, use of pharmaceutical agents that require long term topical or systemic applications at regular and frequent intervals may likely be associated with non-compliance and non-adherence to medication regimens leading to reduced myopia control efficacy. Thus, in addition to use of muscarinic antagonists for myopia control there is a need to provide, sustain, maintain and/or improve efficacy with other avenues. In this regard, there is some evidence that there may be an improved efficacy with combination treatments involving ophthalmic lenses and muscarinic antagonists rather than ophthalmic lenses alone or anti-muscarinic treatments alone. Furthermore, although both muscarinic receptor antagonists and other pharmaceutical agents such as adenosine receptor antagonists may be prescribed for slowing myopia, there is still a need to provide a concurrent/concomitant ophthalmic device such as a spectacle or a contact lens to correct the myopia induced blurred vision at distance. Thus, there is a need to provide an improved ophthalmic lens that is configured to be used in conjunction with one or more pharmaceutical agents (e.g., Atropine) for slowing myopia.

Figure 2B:
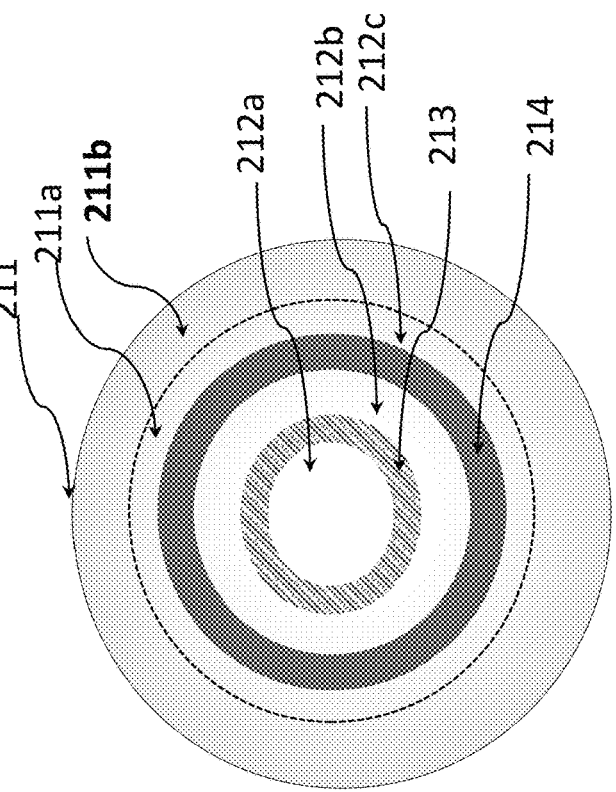
FIG. 2B is a schematic of an ophthalmic lens (e.g., a contact lens) for use in conjunction with pharmaceutical agents for myopia progression.
Figure 2A:
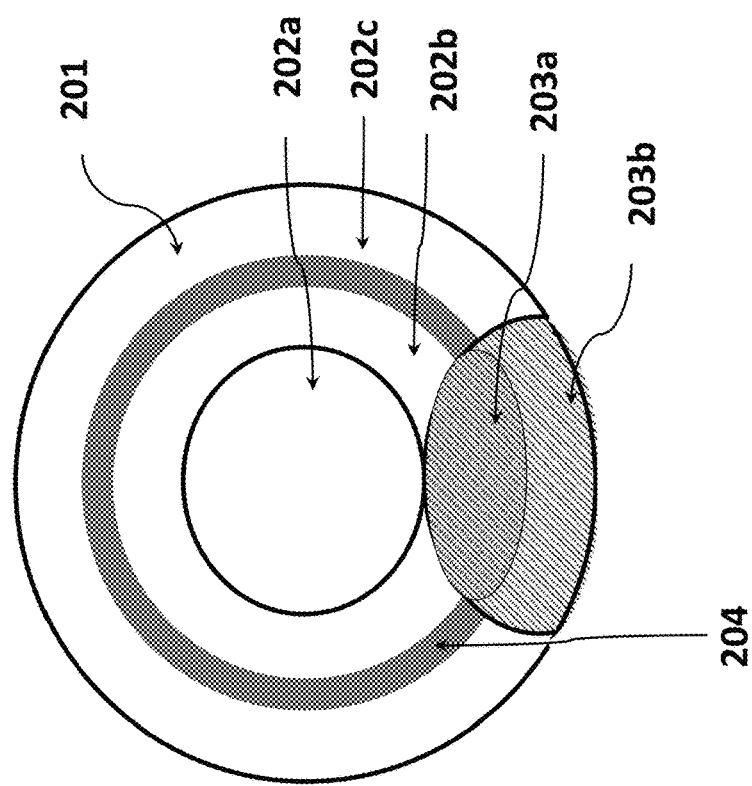
FIG. 2A is a schematic of an ophthalmic lens (e.g., a spectacle lens)

FIG. 2A is a schematic of an embodiment of an ophthalmic lens 201, e.g., a spectacle lens for use in conjunction with a pharmaceutical agent for myopia. In some embodiments, the ophthalmic lens may be a spectacle lens that comprises a base lens with a front surface and a back surface. The ophthalmic lens may have one or more myopia control elements 204 that may be present on one and/or both front and back surfaces, in between the surfaces and/or may be incorporated in the base lens 201 to control, arrest, retard and/or slow myopia. The lens may have one or more first viewing regions (202a, 202b, 202c) wherein, at least part of the viewing regions have a power profile that substantially corrects for the refractive error of the eye for distance. At least one of the first viewing regions 202a is further designed to substantially or significantly minimize, reduce and/or eliminate vision disturbances. The first viewing regions 202a may be substantially aligned with the pupillary axis or the visual axis of the eye when the eye is viewing targets at one or more of far distances. Furthermore, at least one or more dimensions of one of the first viewing regions 202a, such as the size (e.g., length/width), shape and/or position/location may be selected based, at least in part, on the concentration of the muscarinic receptor antagonist (e.g., Atropine or Atropine related compound). In some embodiments, at least one of the first viewing regions 202a, may incorporate a power profile control, reduce or minimize one or more of higher order aberrations resulting from an increase in the pupillary diameter and may be selected based, at least in part, on the concentration of the muscarinic receptor antagonist (e.g., Atropine or Atropine related compound). In some embodiments, the lens may have one or more second viewing regions (203a, 203b). At least one of the second viewing regions 203a may be placed about inferiorly to the first viewing region 202a and has a dioptric power profile that is relatively more positive compared to the dioptric power of the first viewing region 202a to enable substantially normal vision for near distances. The dimensions (e.g., size) and/or the relatively more positive power of at least one or more of the second viewing region 203a and 203b may be selected based, at least in part, on the concentration of the muscarinic receptor antagonist (e.g., Atropine or Atropine related compound) to be used in conjunction with the ophthalmic lens. In some embodiments at least one of the second viewing regions 203a and 203b, may incorporate a power profile to control, reduce and/or minimize one or more of higher order aberrations resulting from an increase in the pupillary diameter and may be selected based, at least in part, on the concentration of the muscarinic receptor antagonist (e.g., Atropine or Atropine related compound). In some embodiments, the dimensions of the one or more first viewing regions 202a and at least one of the second viewing regions 203a may be based upon the pupillary diameter of the eye resulting from the use of the muscarinic receptor antagonist (e.g., Atropine or Atropine related compound) and additionally, the dioptric power profile that results in a relatively more positive power of the at least one of the second viewing regions 203a may be based, at least in part, on the amplitude of accommodation of an eye of an individual resulting from the use of a particular concentration of the muscarinic receptor antagonist (e.g., Atropine or Atropine related compound). In some embodiments, the dimension(s), arrangement, dioptric power, type and/or fill factor of the one or more myopia control elements 204 to slow myopia may be configured based, at least in part, on the concentration of the Atropine or Atropine related compounds in use. In some embodiments, the dimension(s), dioptric power, arrangement, type and/or fill factor of the one or more myopia control elements 204 to slow myopia may be configured based, at least in part, on the concentration of the Atropine or Atropine related compounds in use and/or the rate of progression of myopia. In some embodiments, the ophthalmic lens 201 may further comprise one or more of a light absorbing filter, light absorbing element, photochromic filter, photo mask and/or a phase shift mask to further reduce, minimize and/or eliminate visual disturbance for the eye and configured based, at least in part, on the concentration of the Atropine or Atropine related compounds in use.

FIG. 2B is a schematic of an embodiment of an ophthalmic lens 211, e.g., a contact lens for use in conjunction with a pharmaceutical agent for myopia. In some embodiments, the ophthalmic lens may be a contact lens that comprises a base lens with a front surface, a back surface, an optical zone 211a and a peripheral zone 211b. The ophthalmic lens may have one or more myopia control elements 214 that may be positioned on the base lens 211 to control, arrest, retard and/or slow myopia. The lens may have one or more first viewing regions (212a, 212b, 212c) wherein, at least part of the viewing regions have a power profile that substantially corrects for the refractive error of the eye for distance. At least one of the first viewing regions 212a may have one or more features, such as size designed to minimize, reduce and/or eliminate vision disturbances and may be selected based, at least in part, on the concentration of the muscarinic receptor antagonist (e.g., Atropine or Atropine related compound). In some embodiments, at least one of the first viewing regions 212a, may incorporate a power profile to control, reduce and/or minimize one or more of higher order aberrations resulting from an increase in the pupillary diameter and may be selected based, at least in part, on the concentration of the muscarinic receptor antagonist (e.g., Atropine or Atropine related compound). The first viewing regions 212a may be substantially aligned with the pupillary axis or the visual axis of the eye when viewing targets at one or more of far distances. In some embodiments, the lens may have one or more second viewing regions (213). The one or more second viewing regions 213 may be placed about concentric-co-axial to the first viewing region 212a and may have a dioptric power profile that is relatively more positive compared to the dioptric power of the first viewing region 212a to enable substantially normal vision for near and/or intermediate distances. The dimensions (e.g., size) and/or the relatively more positive power of at least one or more of the second viewing regions 213 may be selected based, at least in part, on the concentration of the muscarinic receptor antagonist (e.g., Atropine or Atropine related compound) to be used in conjunction with the ophthalmic lens. In some embodiments at least one of the second viewing regions 213, may incorporate a power profile to control, reduce and/or minimize one or more of higher order aberrations resulting from an increase in the pupillary diameter and may be selected based, at least in part, on the concentration of the muscarinic receptor antagonist (e.g., Atropine or Atropine related compound). In some embodiments, the location and dimensions of the one or more first viewing regions 212a and the second viewing region 213 may be based upon the pupillary diameter of the eye resulting from the use of the muscarinic receptor antagonist (e.g., Atropine or Atropine related compound) and the dioptric power profile that results in a relatively more positive power of the second viewing region 213 may be based, at least in part, on amplitude of accommodation of an eye of an individual resulting from use of a particular concentration of the muscarinic receptor antagonist (e.g., Atropine or Atropine related compound). In some embodiments, the dimension(s), arrangement, dioptric power, location, type and/or fill factor of the one or more myopia control elements 214 to slow myopia may be configured based, at least in part, on the concentration of the Atropine or Atropine related compounds in use. In some embodiments, the dimension(s), dioptric power, arrangement, location, type and/or fill factor of the one or more myopia control elements 214 to slow myopia may be configured based, at least in part, on the concentration of the Atropine or Atropine related compounds in use and/or the rate of progression of myopia. In some embodiments, the ophthalmic lens 201 may further comprise one or more of a light absorbing filter, light absorbing element, photochromic filter, photo mask and/or a phase shift mask to further reduce, minimize and/or eliminate visual disturbance for the eye and configured based, at least in part, on the concentration of the Atropine or Atropine related compounds in use.

Figure 3:
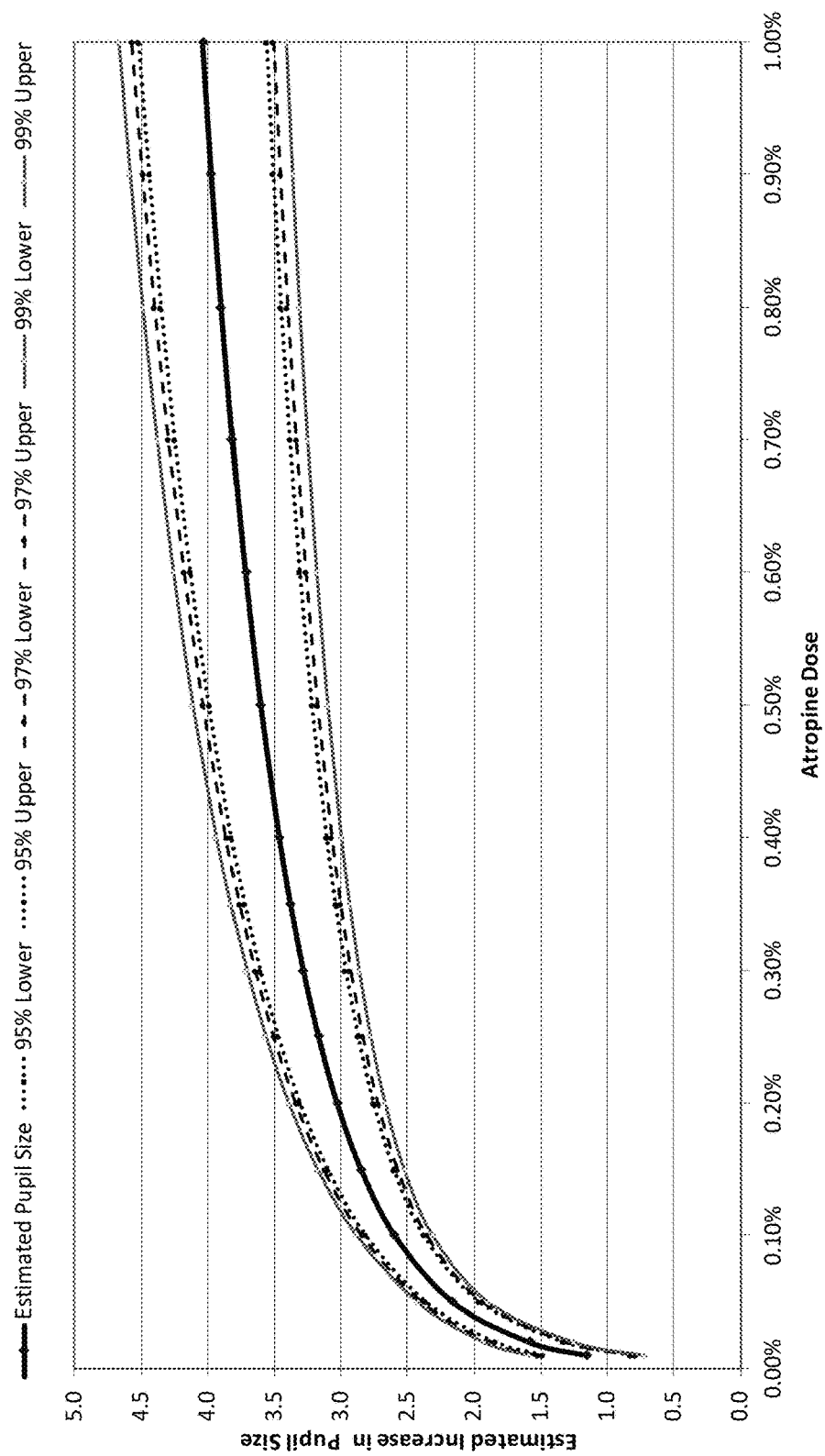
FIG. 3 is a graph illustrating the estimated change in pupil diameter with Atropine concentrations ranging from 0.01% to 1.0%. Data obtained from use of 0.01% to 0.5% Atropine from published studies was used to estimate the pupil diameter; data was additionally extrapolated to 1.0%. Also provided are the 95%, 97% and 99% confidence intervals.
Figure 4:
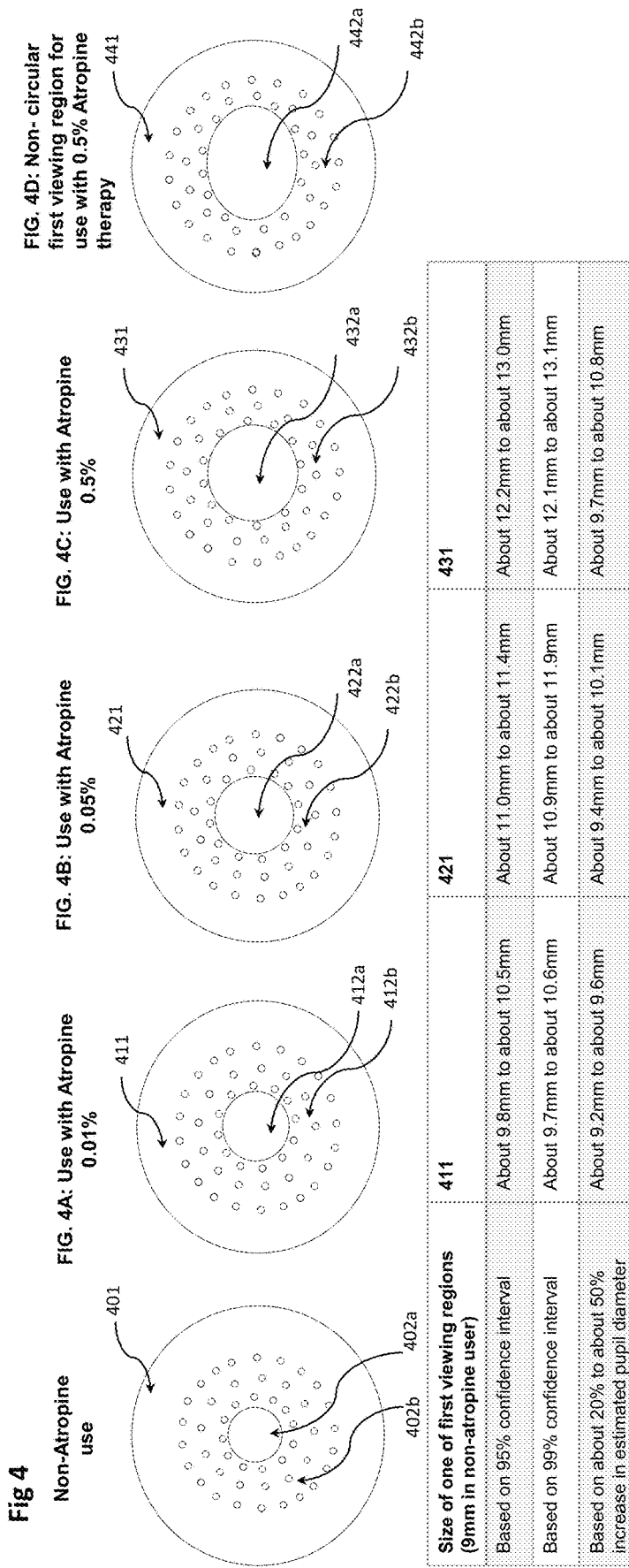
FIG. 4 illustrates an ophthalmic lens, a spectacle lens with myopia control features for use in conjunction with various concentrations of Atropine for slowing myopia.

FIG. 3 illustrates the estimated increase in pupil diameter (derived from pupil sizes provided in FIG. 1) with various concentrations of Atropine and the 95%, 97% and 99% confidence intervals for each of these concentrations. The estimated increase in pupil diameter is provided by the equation "Estimated increase in pupil diameter=6.924+ 0.6266*LN (Concentration of Atropine %/100)" wherein LN is the natural log function. The selection of the dimension(s) such as size and/or shape, and incorporation of aberration control for at least one of the one or more first viewing regions of the ophthalmic lens may be derived based on the estimated change in pupil diameter with a particular concentration of Atropine or Atropine related compound. This is further illustrated in FIG. 4. In some embodiments, the ophthalmic lens may be a spectacle lens. In some embodiments, the dimension of at least one (412a) of the one or more first viewing regions (412a, 412b) of the spectacle lens 411 of FIG. 4 may be a range chosen based on the 95% interval of the equation "Distance(first) viewing region size for normal non-atropine wearer+6.924+ 0.6266*LN (Concentration of Atropine %/100)" wherein LN is the natural log function. If the diameter of the at least one of the first viewing regions 402a of the spectacle lens 401 was 9.0 mm for a user without Atropine therapy, the diameter of the at least one of the first viewing regions 412a of the spectacle lens 411 to be used in conjunction with 0.01% Atropine (FIG. 4A) may vary from about 9.8 mm to about 10.5 mm. In some embodiments, the dimension of at least one of the first viewing regions may be a range chosen based on the 99% confidence interval of the equation "Distance(first) viewing region size for normal non-atropine wearer+6.924+0.6266*LN (Concentration of Atropine %/100)" wherein LN is the natural log function. Therefore, as illustrated in FIG. 4, if the diameter of at least one of the first viewing regions 402a of the spectacle lens 401 for a user without Atropine therapy was 9.0 mm, the diameter of at least one of the first viewing regions 412a of the spectacle lens 411 to be used in conjunction with 0.01% Atropine (FIG. 4A) may vary from about 9.7 mm to about 10.6 mm.

Similarly, if the diameter of the at least one of the first viewing region 402a of the spectacle lens 401 was 9.0 mm for a user without Atropine therapy, the diameter of the first (e.g., distance) viewing region 422a in conjunction with 0.05% Atropine (FIG. 4B) may vary from about 11.0 to about 11.4 mm (95% confidence interval) or about 10.9 mm to 11.9 mm (99% confidence interval). Similarly, if the diameter of at least one of the first viewing regions 402a of the spectacle lens 401 was 9.0 mm for a user without Atropine therapy, the diameter of the at least one of the first viewing regions 432a in conjunction with 0.5% Atropine (FIG. 4C) may vary from about 12.2 to about 13.0 mm (95% confidence interval) or about 12.1 mm to 13.1 mm (99% confidence interval). In some embodiments, the dimension of at least one (412a) of the one or more first viewing regions (412a, 412b) of the spectacle lens 411 of FIG. 4 may be selected based the size of the first viewing region for a normal non-atropine wearer combined with a percentage value of the estimated pupillary diameter as determined using the equation "Estimated increase in pupil diameter=6.924+0.6266*LN (Concentration of Atropine %/100).)". In some embodiments, the size of the first viewing region for a normal non-atropine wearer combined with about 20% of the estimated increase in pupil diameter may be considered to select the dimension of at least one of the first viewing regions (412a of lens 411). In other embodiments, a percentage value of the estimated pupil diameter that is selected may be about 25%, about 30%, about 35%, about 40%, about 45%, about 50%, about 55%, about 60%, about 65%, about 70%, about 75%, about 85%, about 90%, about 15% to about 50%, about 20% to about 60% or about 25% to about 75%. In some embodiments if the diameter of at least one of the first viewing region 402a of the spectacle lens 401 was 9.0 mm for a user without Atropine, then in some embodiments, the diameter of at least one of the first viewing regions 412a of the spectacle lens 411 to be used in conjunction with 0.01% Atropine (FIG. 4A) is based on an about 20% to 50% increase in the estimated pupil size, it may vary from about 9.23 mm to about 9.58 mm.

In some embodiments, the size of at least one of the one or more first viewing regions of the spectacle lens for a user with Atropine therapy may vary from about 4 mm to about 11 mm. In some embodiments, the shape of at least one of the one or more first viewing regions of the spectacle lens for a user with Atropine therapy may be circular. In some embodiments, at least one of the one or more first viewing regions of the spectacle lens for a user with Atropine therapy may be non-circular and may be based on the direction of gaze of the wearer. For example, in certain embodiments, at least one of the one or more first viewing regions may be horizontally oval (442a in FIG. 4D). In such situations, the shorter of the two lengths may be chosen to be at least the length based on the concentration of Atropine as described above and the remainder of the two lengths, may be determined based on the horizontal eye movements of the user and/or derived from population averages of horizontal eye movements. For example, if the eye movements span across 12 mm in the horizontal meridian but only 9 mm in the vertical meridian, then if the diameter of at least one of the first viewing regions 442a of the ophthalmic lens 441 was 9 mm for a user without Atropine therapy, the vertical length of the at least one of the first viewing regions 442a in conjunction with 0.5% atropine (FIG. 4D), may vary from about 12.2 mm to about 13.1 mm. In some embodiments, it may be at least 12.2 mm. In some embodiments, it may be at least 13.1 mm. In some embodiments, based on population averages of eye movements and the concentration of muscarinic receptor antagonist (e.g., Atropine or Atropine related compound), the size of one of one or more first viewing regions of lenses 411 to 441 may be in the range of about 3 mm to about 20 mm, or 5 mm to 15 mm, or 8 mm to 12 mm In some embodiments, the size of one of one or more first viewing regions may range from about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mms, about 18 mms and about 19 mm. In some embodiments, one of the lengths of one of one or more first viewing regions may range from about 4 mm to about 15 mm. In some embodiments, one of the lengths of one of one or more first viewing regions may range from about 8 mm to about 11 mm. In some embodiments, the shape of one of the first viewing regions that is based, at least in part, on the concentration of the muscarinic receptor antagonist (e.g., Atropine or Atropine related compound) may be circular, non-circular, elliptical, oval, square, hexagonal or any other suitable shape and a combination thereof, and when in use, may be positioned symmetrically around one or more axes of the eye (visual axis, pupillary axis, optical axes) or may be positioned asymmetrically around one or more axes of the eyes.

In some embodiments, at least one of the first viewing regions may incorporate a power profile to control, reduce and/or minimize one or more of higher order aberrations resulting from an increase in the pupillary diameter and may be selected based, at least in part, on the concentration of the muscarinic receptor antagonist (e.g., Atropine or Atropine related compound). In some embodiments, at least one of the first viewing regions (412a, 422a, 432a,442a) may incorporate a power profile to control, reduce and/or minimize one or more of a third order aberration, fourth order aberration, fifth order aberration, sixth higher order aberration, other higher order aberrations or a combination of one or more thereof resulting from an increase in the pupillary diameter and may be selected based, at least in part, on the concentration of the muscarinic receptor antagonist (e.g., Atropine or Atropine related compound). In some embodiments, at least one of the first viewing regions (412a, 422a, 432a,442a) may incorporate a power profile to control, reduce and/or minimize one or more of third order aberrations. In some embodiments, at least one of the first viewing regions (412a, 422a, 432a,442a) may incorporate a power profile to control, reduce and/or minimize one or more of fourth order aberrations. In some embodiments, at least one of the first viewing regions (412a, 422a, 432a,442a) may incorporate a power profile to control, reduce and/or minimize one or more of coma, primary spherical aberration, secondary spherical aberration and/or a combination thereof. In some embodiments the control, reduction, minimization of one or more of the higher order aberrations may be derived from a surface curvature generated by a conic section, or utilizing other complex surfaces incorporating one or more of Zernicke polynomials, superconics or a combination thereof. Considering the −2.00D myope of example of FIG. 1A, the effective increase of the spherical aberration of the combined spectacle lens and eye system due to an increase in pupillary diameter from about 3 mm to about 6 mm with the use of Atropine was determined to be about +0.50D. The eye of the myope of FIG. 1A may be managed with one of the ophthalmic lens 411, 421 431 illustrated in FIG. 4. The ophthalmic lens of FIG. 4 (411, 421, 431) has at least one first viewing region (412a, 422a, 432a) with a first power profile to correct the distance refractive error and the first power profile may be selected based, at least in part, on the concentration of the pharmaceutical agent in use. The first power profile selected to correct for the increased spherical aberration of +0.50D from the combined eye and optical system due to the increased pupillary diameter may be derived from a surface curvature generated by a conic section, as follows;
the z-coordinate of the surface s given by:

$$z = \frac{cr^2}{1 + \sqrt{1-(1+k)c^2r^2}}$$

where c is the curvature (the reciprocal of the radius), r is the radial coordinate in lens units and k is the conic constant. In other embodiments the control, reduction, minimization of one or more of the higher order aberrations may be derived from a surface curvature generated by a conic section, or utilizing other complex surfaces incorporating one or more of Zernicke polynomials, superconics or a combination thereof.

Figure 5:
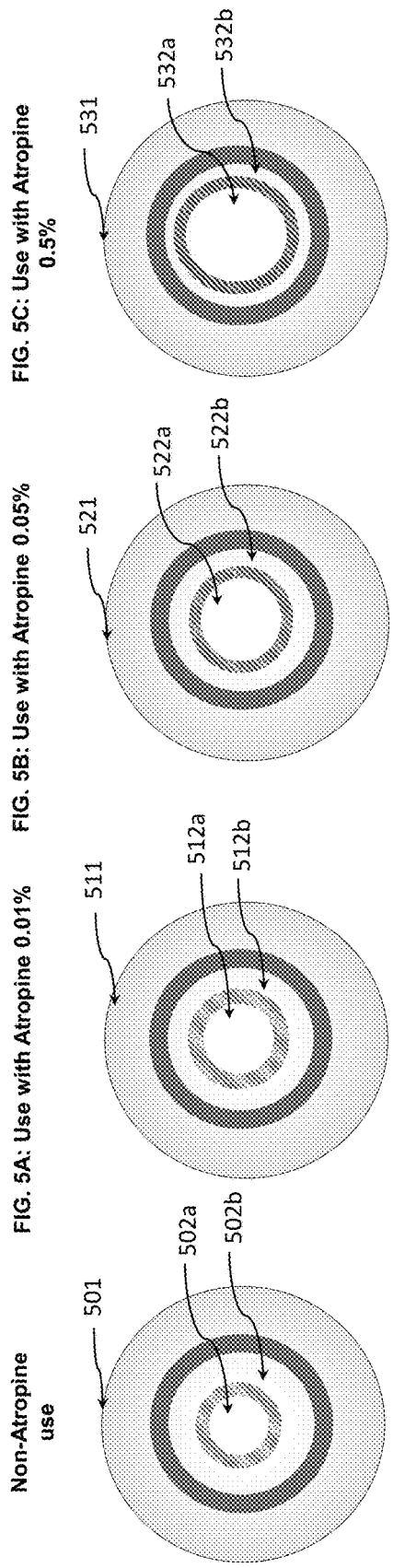
FIG. 5 illustrates an ophthalmic lens, a contact lens with myopia control features for use in conjunction with various concentrations of Atropine for slowing myopia.

In some embodiments, the ophthalmic lens may be a contact lens. The lens may have one or more first viewing regions (502a, 502b of lens 501 as illustrated in FIG. 5) with a dioptric focal power that corrects for the refractive error of the eye for distance. The selection of one or more dimensions such as the size, shape and/or incorporation of aberration control of at least one of the one or more first viewing regions of the contact lens may be derived based on the estimated change in pupil diameter with a particular concentration of Atropine or Atropine related compound. In some embodiments, the dimension (e.g., size) of at least one of the one or more first viewing regions located centrally 502 may be a range chosen based on the 95% interval of the equation "(6.924+0.6266*LN (Concentration of Atropine %/100))". If the diameter of one of the first viewing regions 502a of the contact lens 501 was 2.0 mm for a user without Atropine therapy, the diameter of the first viewing regions 512a of the contact lens 511 used in conjunction with 0.01% Atropine (FIG. 5a) and based on 95% confidence interval may vary from about 2.8 mm to about 3.5 mm. In some embodiments, the diameter of the first viewing regions 512a may vary from about 2.2 mm to about 4.0 mm (or as much as 10 mm to 11 mm when the non-atropine first viewing region is between 6 mm to about 8 mm). Similarly, when used in conjunction with 0.05% atropine, the diameter of the first viewing region 522a of contact lens 521 may vary from about 4.0 mm to about 4.4 mm and when used in conjunction with 0.5% atropine may vary from about 5.2 mm to about 6.0 mm (first viewing zone 532a of contact lens 531). Similarly, if the diameter of one of the first viewing regions 502a of the contact lens 501 was 2.0 mm for a user without Atropine therapy, the diameter of the first viewing regions 512a of the contact lens 511 used in conjunction with 0.01% Atropine (FIG. 5a) and based on 99% confidence interval may vary from about 2.7 mm to about 3.6 mm. Similarly, when used in conjunction with 0.05% atropine, the diameter of the first viewing region 522a of contact lens 521 may vary from about 3.9 mm to about 4.9 mm and when used in conjunction with 0.5% atropine may vary from about 5.1 mm to about 6.1 mm (first viewing zone 532a of contact lens 531).

In some embodiments, the dimension of at least one of the one or more first viewing regions (512a, 512b) of the contact lens 511 of FIG. 5 may be selected based on the size of the first viewing region for a normal non-atropine wearer combined with a percentage value of the estimated pupillary diameter as determined using the equation "Estimated increase in pupil diameter=6.924+0.6266*LN (Concentration of Atropine %/100)".)" wherein LN is the natural log function. In some embodiments, about 10% to 20% of the estimated increase in pupil diameter may be considered to select the dimension of at least one of the first viewing regions (512a of lens 511). In other embodiments, a percentage value of the estimated pupil diameter that is selected may be about 15%, about 20%, 25%, about 30%, about 35%, about 40%, about 45%, about 50%, about 55%, about 60%, about 65%, about 70%, about 75%, about 85%, about 90%, about 15% to about 50%, about 20% to about 60% or about 25% to about 75%. In some embodiments if the diameter of at least one of the first viewing region 502a of the contact lens 501 was 2.0 mm for a user without Atropine, then in some embodiments, the diameter of at least one of the first viewing regions 512a of the contact lens 511 to be used in conjunction with 0.01% Atropine (FIG. 5A) is based on an about 20% to 50% increase in the estimated pupil size, it may vary from about 2.23 mm to about 2.58 mm.

In some embodiments, at least one of the first viewing regions may incorporate a power profile to control, reduce and/or minimize one or more of higher order aberrations resulting from an increase in the pupillary diameter and may be selected based, at least in part, on the concentration of the muscarinic receptor antagonist (e.g., Atropine or Atropine related compound). In some embodiments, at least one of the first viewing regions (512a, 522a, 532a) may incorporate a power profile to control, reduce or minimize one or more of a third order aberration, fourth order aberration, fifth order aberration, sixth higher order aberration, other higher order aberrations or a combination thereof resulting from an increase in the pupillary diameter and may be selected based, at least in part, on the concentration of the muscarinic receptor antagonist (e.g., Atropine or Atropine related compound). In some embodiments, at least one of the first viewing regions (512a,522a,532a) may incorporate a power profile to control, reduce or minimize one or more of a third order aberration. In some embodiments, at least one of the first viewing regions ((512a,522a,532a) may incorporate a power profile to control, reduce or minimize one or more of a fourth order aberration. In some embodiments, at least one of the first viewing regions (512a, 522a, 532a) may incorporate a power profile to control, reduce or minimize one or more of coma, primary spherical aberration, secondary spherical aberration and/or a combination thereof.

In some embodiments, the shape of one of the first viewing regions that is based, at least in part, on the concentration of the muscarinic receptor antagonist (e.g., Atropine or Atropine related compound) may be circular, non-circular, elliptical, oval, hexagonal or any other suitable shape and combinations of one or more thereof and when in use, may be positioned symmetrically around one or more axes of the eye (e.g., visual axis, pupillary axis, optical axes) or may be positioned asymmetrically around one or more axes of the eyes.

In some embodiments, the size of at least one of the one or more first viewing regions of the spectacle lens to be used in conjunction with atropine or atropine related compounds may be about 4% to about 95% larger (e.g., about 5%, 10%, 15%, 20%, 25%, 30%, 35%, 40%, 45%, 50%, 55%, 60%, 65%, 70%, 75%, 80%, 85%, 90%, or 95% larger) compared to the size of the corresponding at least one of the one or more first viewing regions without the use of atropine. In some embodiments, the size of at least one of the one or more first viewing regions of the spectacle lens to be used in conjunction with atropine or atropine related compounds in concentrations <0.05% may be about 4% to about 60% larger (e.g., about 5%, 10%, 15%, 20%, 25%, 30%, 35%, 40%, 45%, 50%, 55%, or 60% larger) compared to the size of the corresponding at least one of the one or more first viewing regions without the use of atropine. In some embodiments, the size of at least one of the one or more first viewing regions of the spectacle lens to be used in conjunction with atropine or atropine related compounds in concentrations=0.05% may be about 20% to about 70% larger (e.g., about 20%, 25%, 30%, 35%, 40%, 45%, 50%, 55%, 60%, 65%, or 70% larger) compared to the size of the corresponding at least one of the one or more first viewing regions without the use of atropine. In some embodiments, the size of at least one of the one or more first viewing regions of the spectacle lens to be used in conjunction with atropine or atropine related compounds in concentrations >0.05% may be about 20% to about 95% larger (e.g., about 20%, 25%, 30%, 35%, 40%, 45%, 50%, 55%, 60%, 65%, 70%, 75%, 80%, 85%, 90%, or 95% larger) compared to the size of corresponding one of the first viewing regions without the use of atropine.

In some embodiments, the size of at least one of the one or more first viewing regions of the contact lens to be used in conjunction with atropine or atropine related compounds may be about 25% to about 400% larger (e.g., about 25%, 50%, 75%, 100%, 125%, 150%, 175%, 200%, 225%, 250%, 275%, 300%, 325%, 350%, 375%, or 400% larger) compared to the size of the corresponding at least one of the one or more first viewing regions without the use of atropine. In some embodiments, the size of at least one of the one or more first viewing regions of the contact lens to be used in conjunction with atropine or atropine related compounds in concentrations <0.05% may be about 25% to about 80% larger (e.g., about 5%, 10%, 15%, 20%, 25%, 30%, 35%, 40%, 45%, 50%, 55%, 60%, 70%, 80% or about 60% larger or about 70% larger) compared to the size of the corresponding at least one of the one or more first viewing regions without the use of atropine. In some embodiments, the size of at least one of the one or more first viewing regions of the contact lens to be used in conjunction with atropine or atropine related compounds in concentrations=0.05% may be about 80% to about 150% larger (e.g., about 80%, 85%, 90%, 95%, 100%, 105%, 110%, 115%, 120%, 125%, 130%, 135%, 140%, 145% or 150% larger) compared to the size of the corresponding at least one of the one or more first viewing regions without the use of atropine. In some embodiments, the size of at least one of the one or more first viewing regions of the contact lens to be used in conjunction with atropine or atropine related compounds in concentrations >0.05% may be about 100% to about 200% larger (e.g., about 100%, 110%, 120%, 130%, 140%, 150%, 160%, 170%, 180%, 190%, 200% larger) compared to the size of corresponding one of the first viewing regions without the use of atropine.

Figure 6:
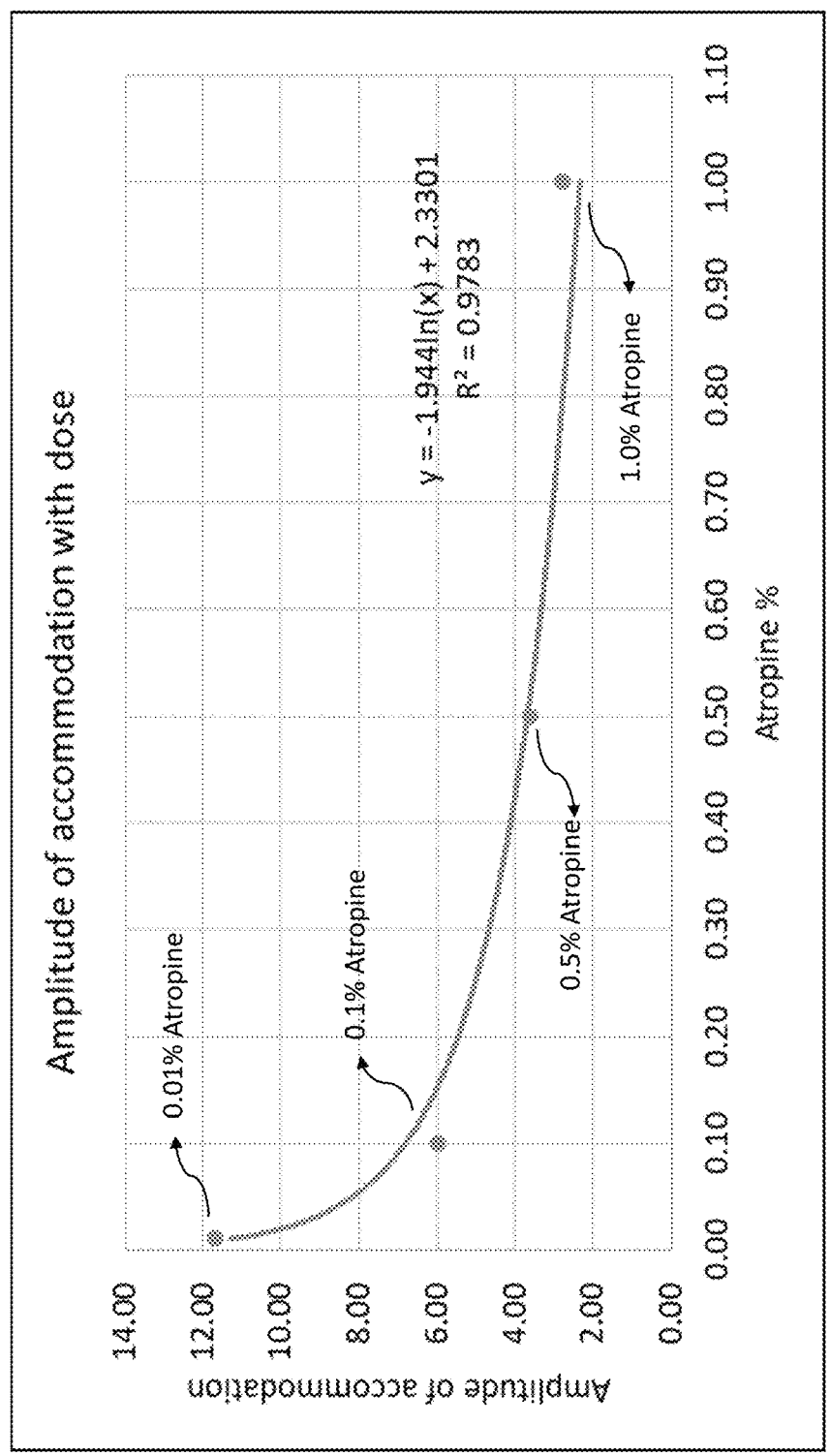
FIG. 6 is a graph based on published data that illustrates the reduction in accommodative amplitude with varying concentrations of Atropine.
Figure 7:
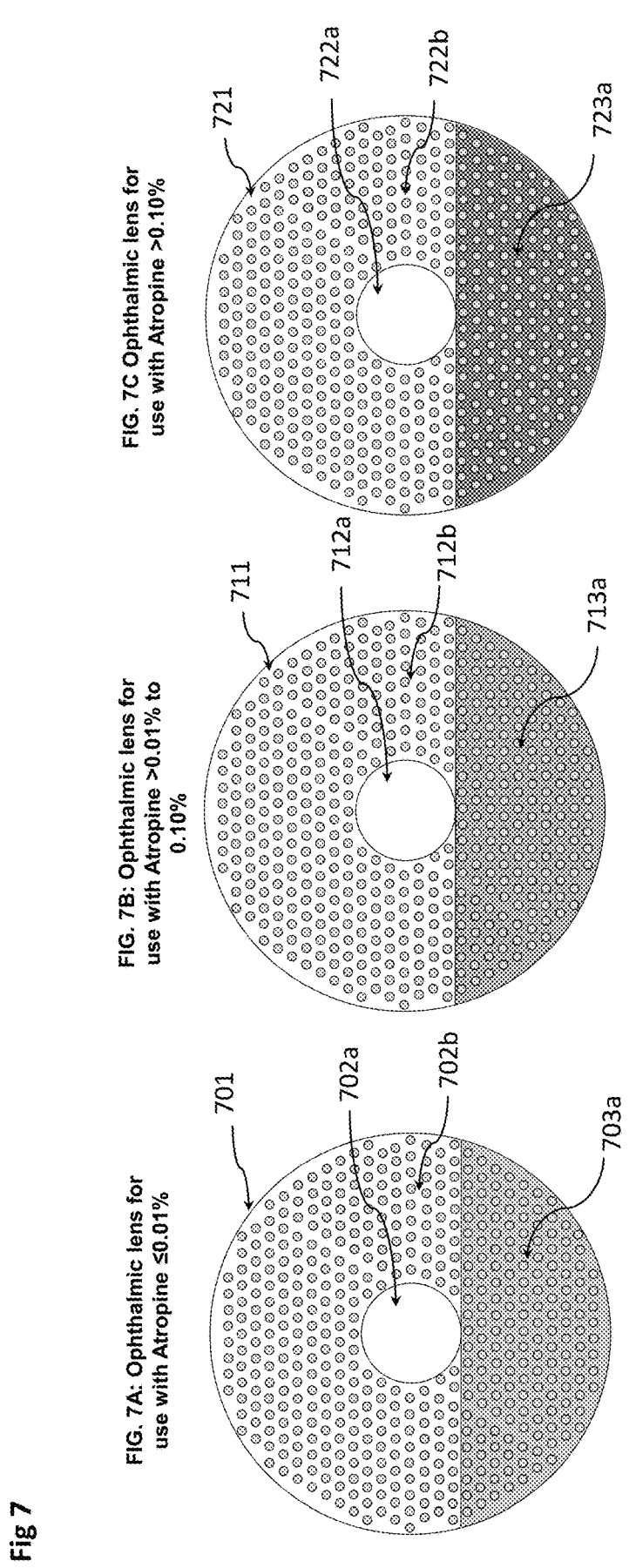
FIG. 7 illustrate a series of ophthalmic lenses with myopia control elements for use in conjunction with Atropine.

FIG. 6 illustrates the decline in amplitude of accommodation with increasing concentrations of Atropine in children aged 6-12 years; concentrations greater than 0.1% Atropine reduce the amplitude of accommodation by more than half. As illustrated in FIG. 7A to 7C, based on the concentration of the Atropine or Atropine related compounds in use, an ophthalmic lens may be selected to provide a relatively more positive power (also referred to as "add power") in one or more of the second viewing regions of the ophthalmic lens compared to the one or more first viewing regions. FIG. 7A illustrates a spectacle lens 701 with one or more first viewing regions 702a and 702b. When used in conjunction with Atropine or Atropine related compound concentrations of ≤0.01%, the spectacle lens has a second viewing region 703a positioned inferiorly relative to first viewing region 702a and has more positive power relative to 702a of about ≤+1.00D. In some embodiments, the relatively more positive power in one or more of the second viewing regions of a spectacle lens that may be used in conjunction with Atropine or Atropine related compound concentrations of ≤0.01% may be about ≤+0.75D. In some embodiments, the relatively more positive power in one or more of the second viewing regions of a spectacle lens that may be used in conjunction with Atropine or Atropine related compound concentrations of ≤0.01% may be about ≤+0.50D. In some embodiments, for use in conjunction with Atropine concentrations ranging from >0.01% to 0.1%, the relatively more positive power (or add power) in the second viewing regions 713a of the ophthalmic lens 711 may be about ≥+1.00D to ≤+2.00D. In some embodiments, for use in conjunction with Atropine concentrations ranging from >0.01% to 0.1%, the relatively more positive power (or add power) in one or more of the second viewing regions may be about ≥+1.25D to ≤+2.00D or ≥+1.25D to ≤+2.50D. In some embodiments, for use in conjunction with Atropine concentrations ranging from >0.01% to 0.1%, the relatively more positive power (or add power) in one or more of the second viewing regions may be about ≥+1.50D to ≤+2.00D. In some embodiments, for use in conjunction with Atropine concentrations greater than 0.1%, as illustrated in FIG. 7C, the relatively more positive power (or add power) in one or more of the second viewing regions 723a of the ophthalmic lens 721 may be about ≥+1.50D or higher. In some embodiments, for use in conjunction with Atropine concentrations greater than 0.1%, the relatively more positive power (or add power) in one of the second viewing regions may be about ≥+2.00D, ≥+2.50D, or higher, may be about ≥+2.00D to about ≤+3.50D, maybe about ≥+1.50D to about ≤+5.00D.

Figure 8:
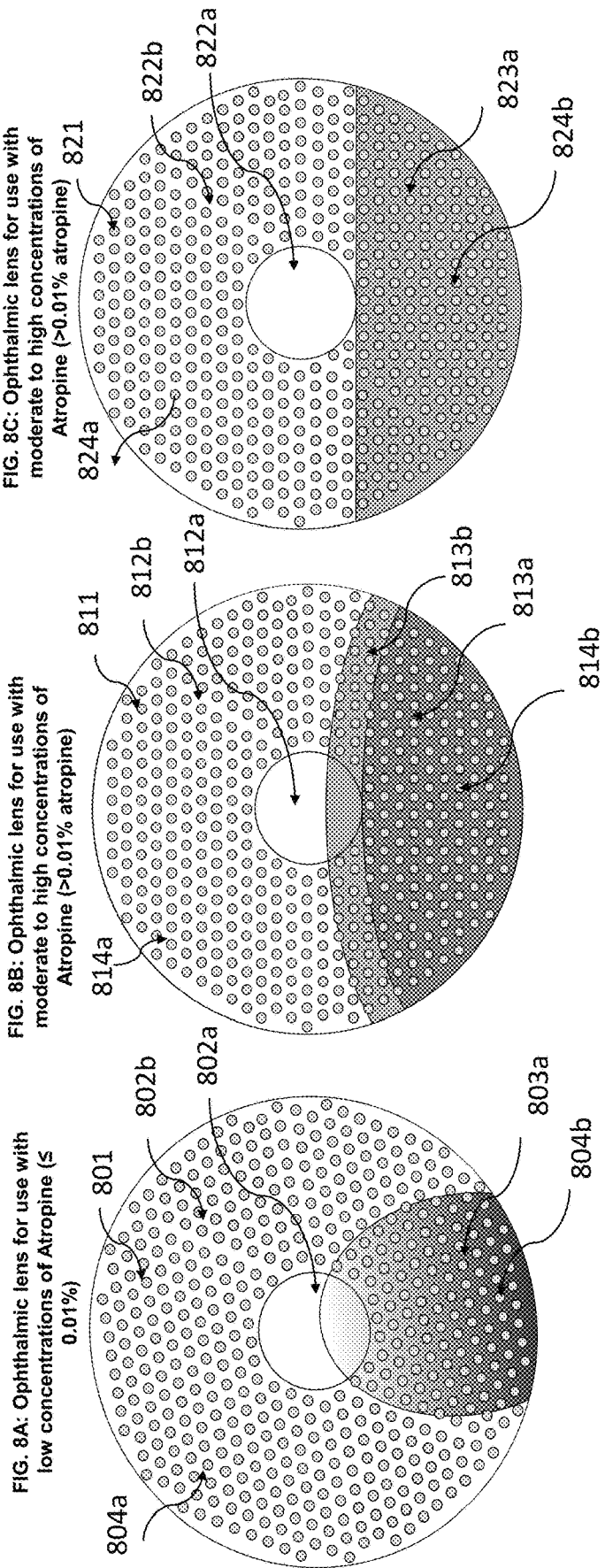
FIG. 8 is a schematic of a series of ophthalmic lenses with myopia control elements for use in conjunction with Atropine and illustrates the dimensions of the one or more second viewing regions selected based on the concentration of the Atropine prescribed for use.

In some embodiments, as illustrated in FIG. 8, the ophthalmic lens may comprise one or more first viewing regions (802a and 802b in lens 801; 812a and 812b in lens 811 and 822a and 822b in lens 821), one or more myopia control elements (804a and 804b in lens 801; 814a and 814b in lens 811 and 824a and 824b in lens 821) and one or more second viewing regions (803a in lens 801; 813a and 813b in lens 811 and 823a in lens 821). The size of at least one of the one or more second viewing regions may be configured at least in part based on the concentration of Atropine or Atropine related compounds. In some embodiments, when used in conjunction with low concentrations of atropine (0.01% or lower), the size of at least one or more of the second viewing regions (803a) may be smaller compared to the size of at least one or more of the second viewing regions used in conjunction with moderate to high concentrations of atropine (>0.01% atropine), as illustrated in FIGS. 8B and 8C by 813a (one of the second viewing regions occupies a larger portion inferiorly) or 823a (the second viewing regions is across substantially across a large portion inferiorly of the lens). In some embodiments, at least one of the second viewing regions may be placed relative to the direction of the primary gaze (or gaze adopted for distance viewing) of the wearer to minimize vision disturbances during intermediate and/or near tasks. As illustrated in FIG. 8A, the second viewing region (803a) is off-set, in an anti-clockwise direction to coincide with the shift in the primary gaze from straight ahead position to a nasal direction for the right eye of an user during near viewing (in some embodiments, the second viewing region (803a) may be off-set, in a clockwise direction to coincide with the shift in the primary gaze in the temporal direction for the right eye of an user during near viewing). In some embodiments, the relatively more positive power in at least one or more of the second viewing regions may be uniformly distributed, as illustrated in region 823a of lens 821 whereas in some embodiments, the power distribution across one or more second viewing regions may have a gradient power, as illustrated in region 803a of lens 801 where the power increases gradually towards the lower region of 803a. In some embodiments, as illustrated in FIGS. 8A and 8B, one of the first viewing regions i.e. 802a of lens 801 and 812a of lens 811 may comprise a dioptric power profile that is relatively more positive in certain areas of the region. Such a lens of FIGS. 8A and 8B may be useful for an individual in an environment that may be limited to near distances, for example children working on computers, or individuals operating in mostly near distance ranges such as on benchtops, laboratories or desk based. Furthermore, as illustrated in FIG. 8A to 8C, in some embodiments, one or more of myopia control elements may be incorporated in at least one or more of the first viewing regions and one or more second viewing regions. In other embodiments, one or more of the second viewing regions may incorporate a power profile to control, reduce and/or minimize one or more of higher order aberrations resulting from an increase in the pupillary diameter and may be selected based, at least in part, on the concentration of the muscarinic receptor antagonist (e.g., Atropine or Atropine related compound).

Many variations of the type, size, arrangement, fill factor and magnitude/strength of the one or more myopia control elements that maybe possible. The below are but a few examples of the types of configurations and fill factors that may be possible. In some embodiments, the myopia control elements may be micro lenses, may be meta lenses or may be a simple variation of the geometric and optical properties of the lens/lens surfaces to induce a refractive power change. In some embodiments, the myopia control elements may be one or more of refractive, diffractive, contrast modulating, phase-modulating, meta-surfaces, light scattering, light-deviating, amplitude modulating, aberrated, holographic, light-diffusing elements, or a combination of one or more elements thereof. In some embodiments, the myopia control elements may be refractive elements designed to impose myopic defocus, hyperopic defocus, create an extended depth of focus, create multifocality or a combination thereof.

Figure 9:
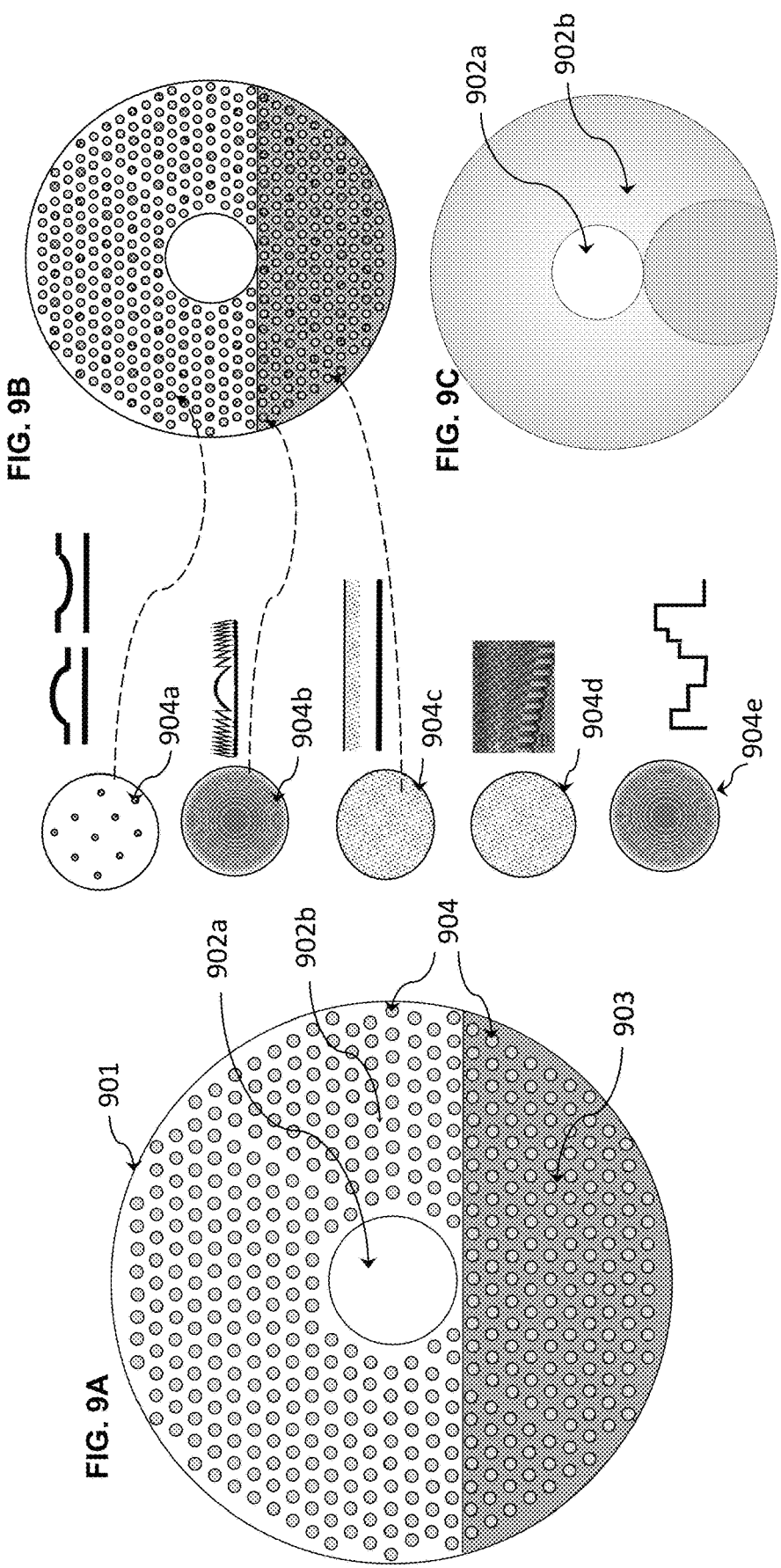
FIG. 9A is a schematic of an ophthalmic lens with myopia control elements for use in conjunction with Atropine or other pharmaceutical agent for myopia with myopia control elements (904a to 904e).
FIG. 9B illustrates an ophthalmic lens with one of the one or more first viewing regions selected based on Atropine concentration; a second viewing region with one of the one or more second viewing regions selected based on Atropine concentration and a plurality of discrete myopia control elements across the ophthalmic lens.
FIG. 9C illustrates an ophthalmic lens with one of the one or more first viewing regions selected based on Atropine concentration; a second viewing region with one of the one or more second viewing regions selected based on Atropine concentration and a myopia control element with a continuous power profile that is relatively more positive than one of the first viewing regions of the ophthalmic lens.

FIG. 9 is a schematic of a spectacle lens 901 used in conjunction with muscarinic receptor antagonist (e.g., Atropine or Atropine related compound) to slow myopia progression. As illustrated in FIG. 9, the lens comprises a plurality of first viewing regions 902a and 902b with at least one feature of 902a selected based, at least in part, on the concentration of muscarinic receptor antagonist (e.g., Atropine or Atropine related compound) in use. The lens further comprises a second viewing region 903 and the myopia control elements 904 may be positioned across one or more first viewing regions and the second viewing region. The myopia control elements 904 may be refractive 904a, diffractive 904b, scatter 904c, meta lenses 904d, phase step 904e, other myopia control elements, and/or may feature any combination of one or more myopia control elements thereof (FIG. 9B). In some embodiments, the myopia control elements may be discrete elements, continuous elements, or a combination. In some embodiments, the discrete myopia control elements may be incorporated as annular ring-shaped elements, part annular ring, arc shaped elements, small circular elements, prismatic elements, or as elements of any other suitable shape and/or any combination of one or more thereof. In some embodiments, the one or more discrete myopia control elements may be positioned apart from the other myopia control elements. In some embodiments, the one or more discrete myopia control elements may be positioned in contact with or conjoined with or fused with one or more of other myopia control elements or a combination thereof. In some embodiments, the refractive elements may be shaped as a circular element, ring, arc, spiral, triangular or any other shape or a combination thereof or as a part-continuous, substantially continuous refractive power profile that may be monotonic, may be non-monotonic, may be periodic, maybe aperiodic or a combination thereof. In some embodiments, the refractive myopia control elements may be designed to provide no defocus, hyperopic defocus, myopic defocus, extended depth of focus, aberrations or a combination thereof compared to refractive power profile in one or more first viewing regions designed to correct for the distance refractive error of the eye. In some embodiments, the myopia control elements may be incorporated as a partially continuous, substantially continuous or continuous change in power profile that may be monotonic, may be non-monotonic, may be periodic, maybe aperiodic or a combination thereof. In FIG. 9C, the ophthalmic lens incorporates a myopia control feature in one of the first viewing regions 902b; the power profile increases in relatively more positive power from the boundary of 902a towards the periphery of the ophthalmic lens. In some embodiments, the myopia control elements may be arranged in a random or a non-random arrangement/pattern.

Figure 10:
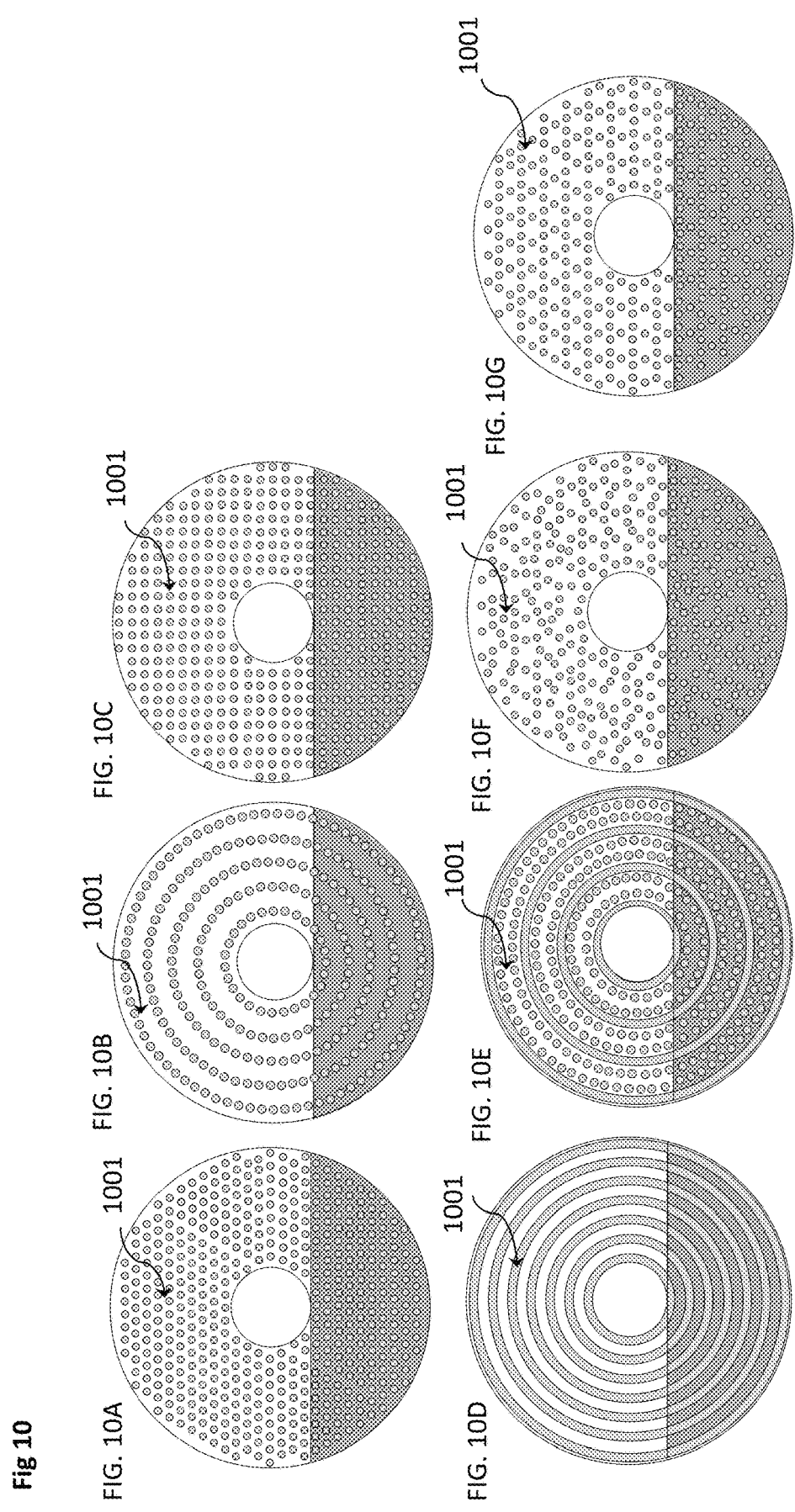
FIG. 10 is a schematic of an ophthalmic lens comprising one or more first viewing regions, one or more second viewing regions and one or more myopia control elements for use in conjunction with Atropine or other pharmaceutical agent for myopia.

In some embodiments, when the arrangement is non-random, they may be placed in a hexagonal, concentric individual, squared, or annular pattern as illustrated in FIG. 10a to 10g or may be any other suitable arrangement or combinations of one or more thereof. In some embodiments, when the arrangement is random, they may be placed in an asymmetrical pattern (FIG. 10g) or in a symmetrical manner (FIG. 10f). In some embodiments, the myopia control elements may be incorporated across one or more of the first viewing regions, across one or more of the second viewing regions or across both regions. In some embodiments, the one or myopia control elements may be positioned across the front surface, the back surface or both the surfaces. In certain embodiments, the one or more myopia control elements may be present across the whole of one or both the surfaces or across part of one or both surfaces or in between the surfaces. In some embodiments, the one or more myopia control elements may be present on about 90% or more of the lens surface, about 85% of lens surface, about 80% of lens surface, about 75% of lens surface, about 70% of lens surface, about 65% of the lens surface, about 60% of lens surface, about 55% of lens surface, about 50% of lens surface, about 45% of lens surface, about 40% of the lens surface, about 35% of the lens surface, about 30% of the lens surface, about 25% of the lens surface, about 20% of the lens surface, about 15% of the lens surface and about 10% of the lens surface. In some embodiments, the one or more myopia control elements may be present in a range varying from about 20% to about 60% (e.g., about 20%, 25%, 30%, 35%, 40%, 45%, 50%, 55%, or 60%). In some embodiments, the myopia control elements may only be incorporated in regions other than one or more of the first viewing regions that may be selected based, at least in part, on the concentration of the muscarinic receptor antagonist (e.g., Atropine or Atropine related compound). In some embodiments, the myopia control elements may only be incorporated in regions other than one or more of the first and one or more of the second viewing regions that may be selected based, at least in part, on the concentration of the muscarinic receptor antagonist (e.g., Atropine or Atropine related compound).

Figure 11:
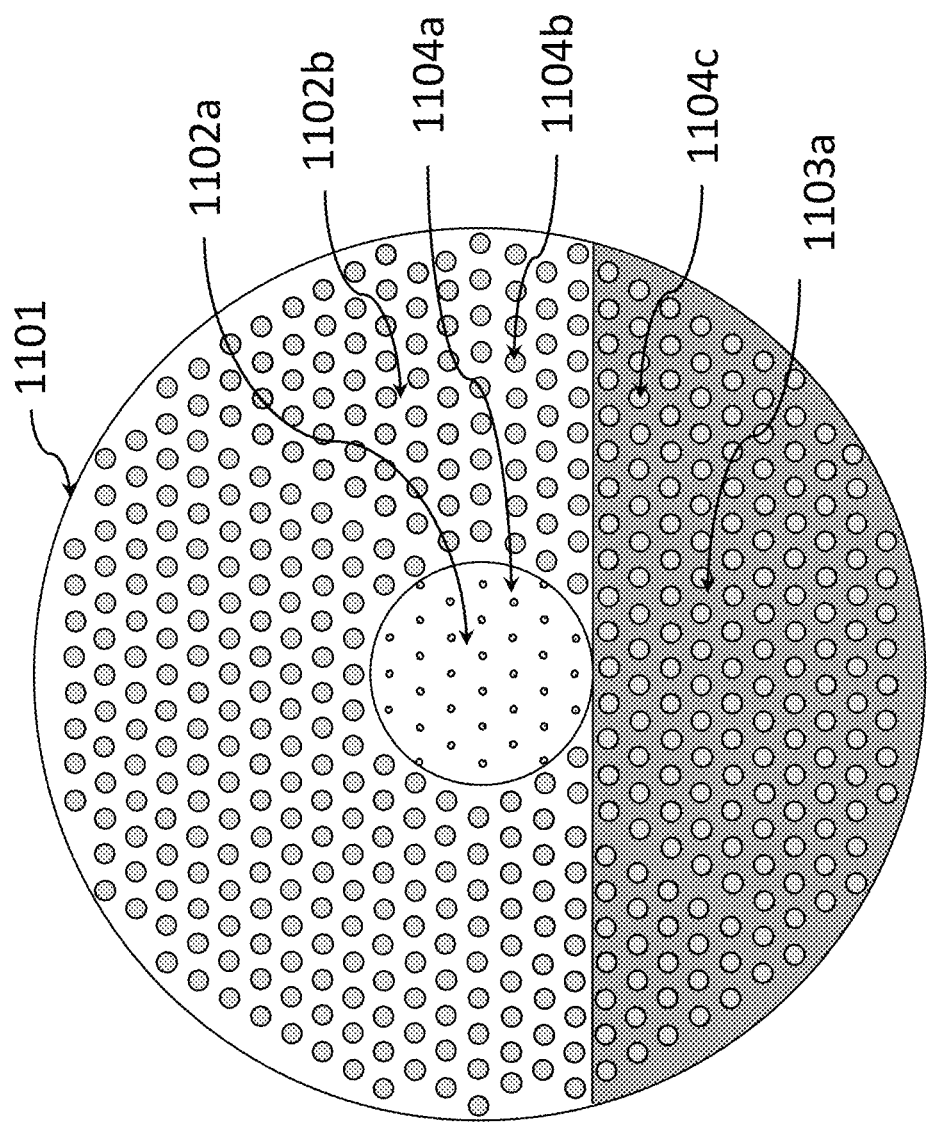
FIG. 11 is a schematic of an ophthalmic lens comprising one or more first viewing regions, one or more second viewing regions and one or more myopia control elements for use in conjunction with Atropine or other pharmaceutical agent for myopia and illustrates the myopia control elements across the lens surface including within the one or more first viewing regions and the one or more second viewing regions.

FIG. 11 is an illustration of a spectacle lens used in conjunction with muscarinic receptor antagonist (e.g., Atropine or Atropine related compound) to slow myopia progression whilst minimizing, reducing and/or eliminating vision disturbances. In FIG. 11, the dimensions of at least one of the first viewing regions 1102a and at least one of the second viewing regions 1103a are sized based, at least in part, on the concentration of the muscarinic receptor antagonist (e.g., Atropine or Atropine related compound) in use. In some embodiments, at least one of the first viewing regions 1102a and/or at least one of the second viewing regions 1103a may incorporate a power profile to control, reduce and/or minimize one or more of higher order aberrations resulting from an increase in the pupillary diameter. Additionally, the dioptric power, i.e., the relatively more positive power of the second viewing region 1103a compared to the first viewing region 1102a is based, at least in part, on the concentration of the muscarinic receptor antagonist (e.g., Atropine or Atropine related compound) in use. Furthermore, the myopia control elements 1104 are present across the entire lens surface including the one or more first viewing regions (1104a, 1104b) and the second viewing region (1104c). In the particular example as illustrated in FIG. 11, the size of the myopia control elements in one of the one or more first viewing regions 1104a is sized smaller in comparison to the myopia control elements across one or more of the other viewing regions of the lens (1104b and 1104c) to reduce and/or minimize visual disturbances when the individual is looking at far distances. In some embodiments, the myopia control elements in one of the one or more first viewing regions 1104a may be sized smaller in comparison to the myopia control elements across one or more of the other viewing regions of the lens (1104b and 1104c) and may be present only in one or more regions of 1102a to control, reduce and/or minimize one or more of higher order aberrations resulting from an increase in the pupillary diameter. Furthermore, in this example, the myopia control elements present across the second viewing region 1104c may be sized larger in comparison to the myopia control elements 1104a in one of the one or more first viewing regions 1102a to ensure that adequate myopia control is provided during near tasks, as excessive near tasks are considered to exacerbate myopia. In some embodiments, the myopia control elements may be one or more of discrete myopia control elements, continuous myopia control elements or a combination thereof. In some embodiments, the strength of the myopia control elements across the second viewing region 1103a may be higher compared to the strength of the myopia control elements across one or more of the distance viewing regions 1102a or 1102b.

In some embodiments, the fill factor of the myopia control elements may vary between the various regions to minimize visual disturbance with the various concentrations of muscarinic receptor antagonist in use and/or maximize myopia control efficacy in conjunction with the muscarinic receptor antagonist in use. In both FIGS. 12A and 12B, one of the first viewing regions 1202a and 1212a are devoid (or substantially devoid) of myopia control elements. Considering another of the first viewing regions 1202b of FIG. 12A, the fill ratio of the myopia control elements (1204a) across this first viewing region 1202b may be less than the fill ratio of the myopia control elements 1204b across the one of the second near viewing regions 1203 and is illustrated in the section 1205c. In FIG. 12B, the fill ratio of the myopia control elements (1214b) across one of the second viewing regions 1213 is less than the fill ratio of myopia control elements 1214a across one of the first viewing regions 1212b, as illustrated in section 1215c. A lesser or greater fill ratio may be achieved based on the size of the myopia control element as illustrated in FIG. 12 or the number of elements e.g., per sq·mm as illustrated in FIG. 13. A lesser fill ratio of myopia control elements in one or more of the first viewing regions and/or one or more of the second viewing regions may be desirable to minimize visual disturbances e.g., with higher concentrations of muscarinic receptor antagonist (e.g., Atropine or Atropine related compounds) whereas a higher fill ratio of myopia control elements in one or more of the first and/or one or more of the second viewing regions may be desirable to aid myopia control with lower concentrations of muscarinic receptor antagonist (e.g., Atropine or Atropine related compounds).

Figure 14:
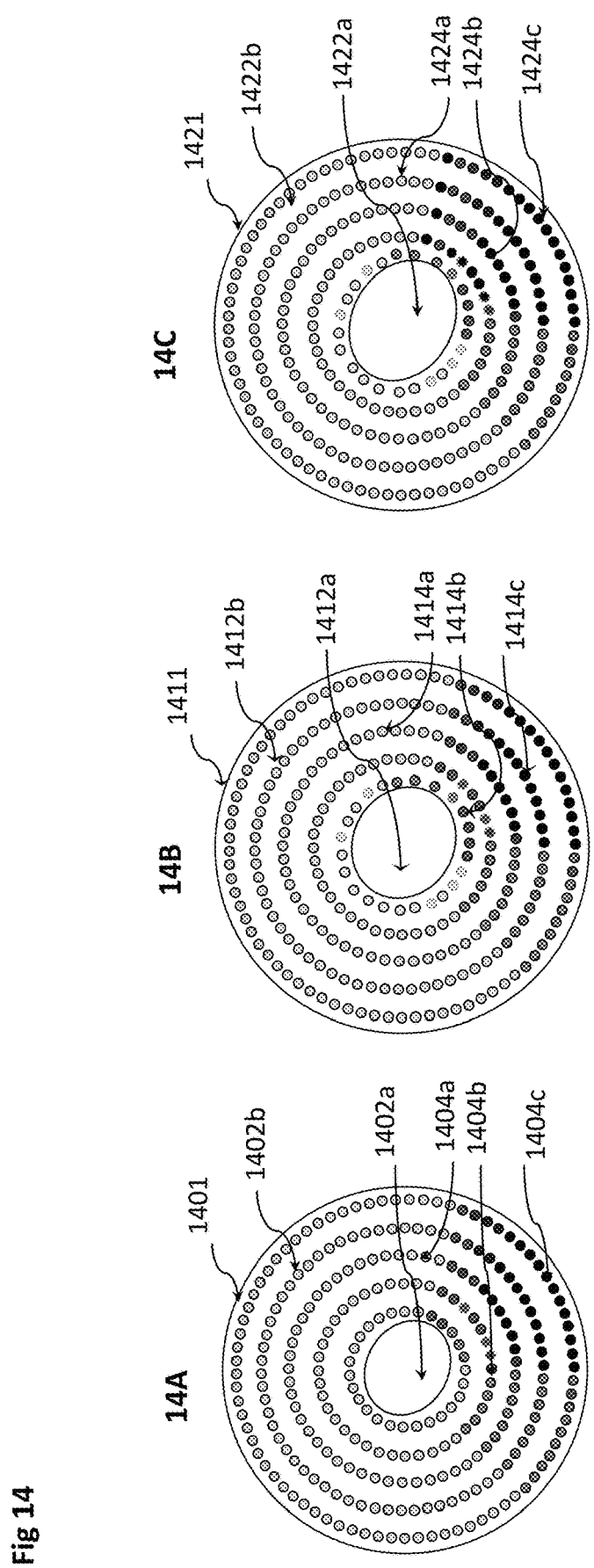
FIG. 14 illustrates a series of ophthalmic lenses, with each lens in the series comprising one of a non-circular first viewing region and one or more myopia control elements across the lens surface except for the non-circular first viewing region for use in conjunction with Atropine or other pharmaceutical agent for myopia. The myopia control elements are refractive elements

FIG. 14 is a schematic of a series of ophthalmic lenses, spectacle lenses used in conjunction with muscarinic receptor antagonist (e.g., Atropine or Atropine related compounds) to slow myopia progression whilst minimizing, reducing and/or eliminating vision disturbances. In FIG. 14, the ophthalmic lenses 1401, 1411 and 1421 are designed to be used in conjunction with low, moderate, and high concentrations of atropine. The dimensions of one of the first viewing regions 1402a, 1412a and 1422a of ophthalmic lenses 1401, 1411 and 1421 are sized based, at least in part, on the concentration of the muscarinic receptor antagonist (e.g., Atropine or Atropine related compound) in use. In some embodiments, at least one of the first viewing regions 1402a, 1412 a and 1422a may incorporate a power profile to control, reduce and/or minimize one or more of higher order aberrations resulting from an increase in the pupillary diameter. The shape of one of the first viewing regions may be non-circular taking into consideration the requirements of the user. In the ophthalmic lens of FIG. 14A, the myopia control elements 1404 are present across the entire lens surface across one of the first viewing regions 1402b and excluding the first viewing region 1402a. The myopia control elements have relatively more positive power (relatively more plus compared to the power in one or more of the first viewing regions 1402a or 1402b) to impose myopic defocus. Since there is accommodative lag for near distances it is preferable to increase the myopic defocus whilst viewing near distances compared to far distances. Thus, to increase and/or maximize the myopia control efficacy, the refractive power or relatively more positive power of the myopia control elements may be arranged such that they gradually increase in relative positive power compared to 1402b from an upper portion of the ophthalmic lens to a lower portion of the ophthalmic lens (relative positive power of 1404c>1404b>1404a) as illustrated in FIG. 14A. Such an arrangement may reduce the risk of visual disturbances for far viewing as the relatively more positive power of the myopia control elements is less for far viewing positions. In the ophthalmic lenses of FIGS. 14B and 14C used in conjunction with higher concentrations of atropine, the sizes of one of the first viewing regions 1412a in FIG. 14B and 1422a in FIG. 14C are larger than 1402a of the lens 1401 drawn in FIG. 14A. Additionally, the strength or relatively more positive power of myopia control elements of the ophthalmic lenses 1411 and 1421 may be higher than the corresponding myopia control elements of ophthalmic lens 1401.

Figure 15:
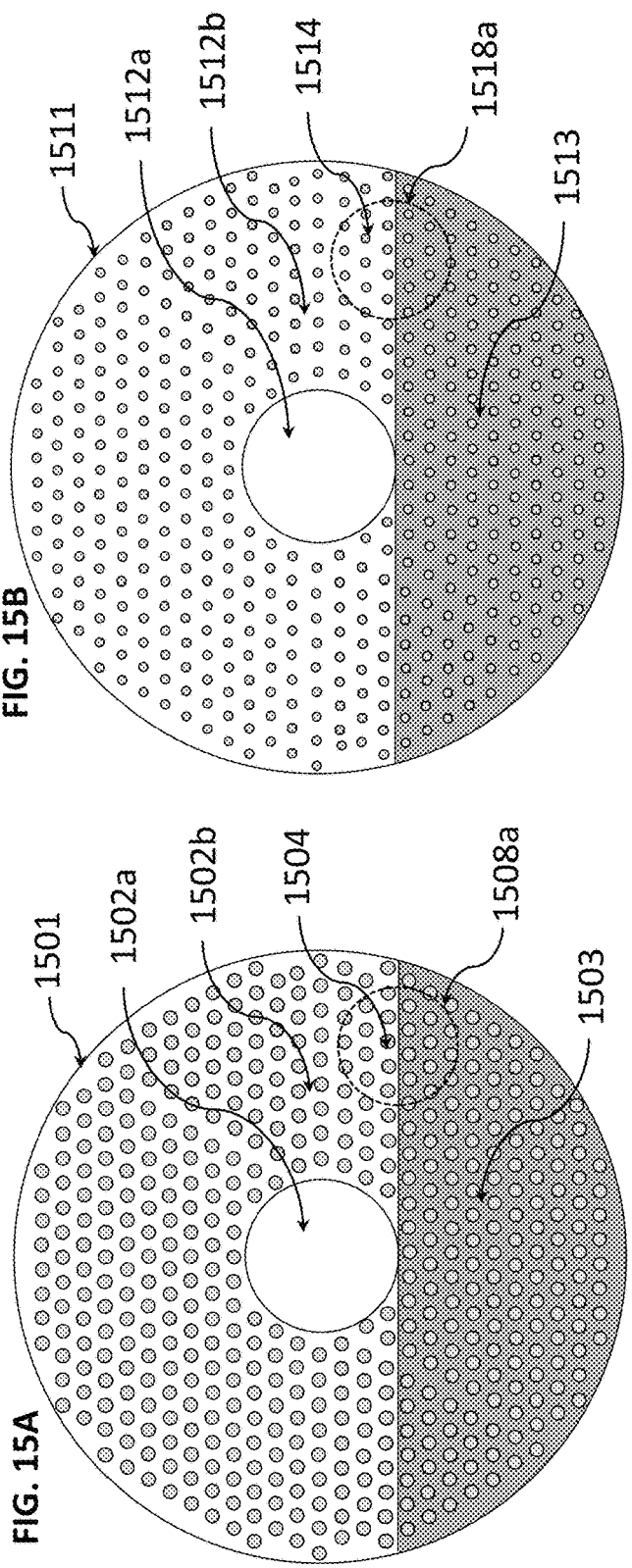
FIG. 15 is a schematic of an ophthalmic lens comprising one or more myopia control elements, one or more first viewing regions and a second viewing region and designed for use in conjunction with Atropine or other pharmaceutical agent for myopia.

FIG. 15 is a schematic of two ophthalmic lenses (1501 and 1511) used in conjunction with muscarinic receptor antagonist (e.g., Atropine or Atropine related compounds) to slow myopia progression whilst minimizing, reducing and/ or eliminating vision disturbances. In FIG. 15A, the dimensions of one of the first viewing region 1502a of lens 1501 is sized based, at least in part, on the concentration of the muscarinic receptor antagonist (e.g., Atropine or Atropine related compound) in use. In some embodiments, at least one of the first viewing regions 1502a, 1512a may incorporate a power profile to control, reduce and/or minimize one or more of higher order aberrations resulting from an increase in the pupillary diameter. Furthermore, the relatively more positive power in the second viewing region (1503) is based, at least in part, on the concentration of the Atropine in use. As illustrated, the myopia control elements (1504) are present across the entire lens surface excluding one of the first viewing regions 1502a. The arrangement of the myopia control elements across one or more of the first viewing regions and one or more of the second viewing regions may be similar across lens 1511. In addition to the concentration of the muscarinic receptor antagonist (e.g., Atropine or Atropine related compound) to be used in conjunction with the ophthalmic lens, the fill ratio of the myopia control elements across the lens may be determined based on the progression of myopia. A higher fill ratio may aid in conjunction with muscarinic receptor antagonist (e.g., Atropine or Atropine related compound) to slow myopia whereas a lower fill ratio may result in lesser visual disturbance. For example, in FIG. 15A, the fill ratio of the myopia control elements across the ophthalmic lens 1501 is >40% (as illustrated in section 1508a) in eyes with a faster than anticipated rate of axial elongation. In eyes where the myopia progression is slower than expected, the fill ratio of the myopia control elements in the lens of 1501 in FIG. 15B may be reduced to <40% (as illustrated in section 1518a). Determination of the rate of progression in order to select the ophthalmic lens to be used in conjunction with the concentration of the muscarinic receptor antagonist (e.g., Atropine or Atropine related compound) may also be made based on history of the individual including age, axial length of the eye, axial length/corneal curvature of the eye, parental myopia, previous progression history and time spent on outdoor and indoor activities.

The ophthalmic lenses described herein can be formed by numerous methods. The ophthalmic lenses or the ophthalmic lens designs described herein may be manufactured using known methods for production of spectacles and contact lenses. In some embodiments, the ophthalmic lens described herein may be manufactured using one or more techniques and/or processes involving molding, lathing, lens surfacing, for example, freeform manufacturing, printing, stamping, coating, encapsulation, additive procedures, subtractive procedures, lasering, etching, photolithography, physical alteration, or a combination of one or more processes or techniques. In some embodiments, the front surface of the ophthalmic lens may be manufactured by molding or casting techniques incorporating one or more myopia control elements, one or more first viewing regions and/or one or more second viewing regions resulting in a semi-finished blank or lens meaning semi-finished blank or lens may require one or more additional processing steps to complete the final lens design to be worn by the individual. For example, one additional processing step may include surfacing and/or polishing the back surface to incorporate the distance refractive error of the eye and may be manufactured using freeform manufacturing processes, lathing or molding or other techniques. In some embodiments, the one or more myopia control elements or the second viewing region may be produced as a separate step to the manufacturing of the lens e.g., by an additive process (such as a 3D printing, inkjet printing or a lens coating or a film encapsulation or a polymer layer step) or a subtractive process (laser) or by altering the physical properties of the lens material such surface finish, refractive index, surface shape or curvature in whole or in part (laser or stamping or compression).

Figure 16:
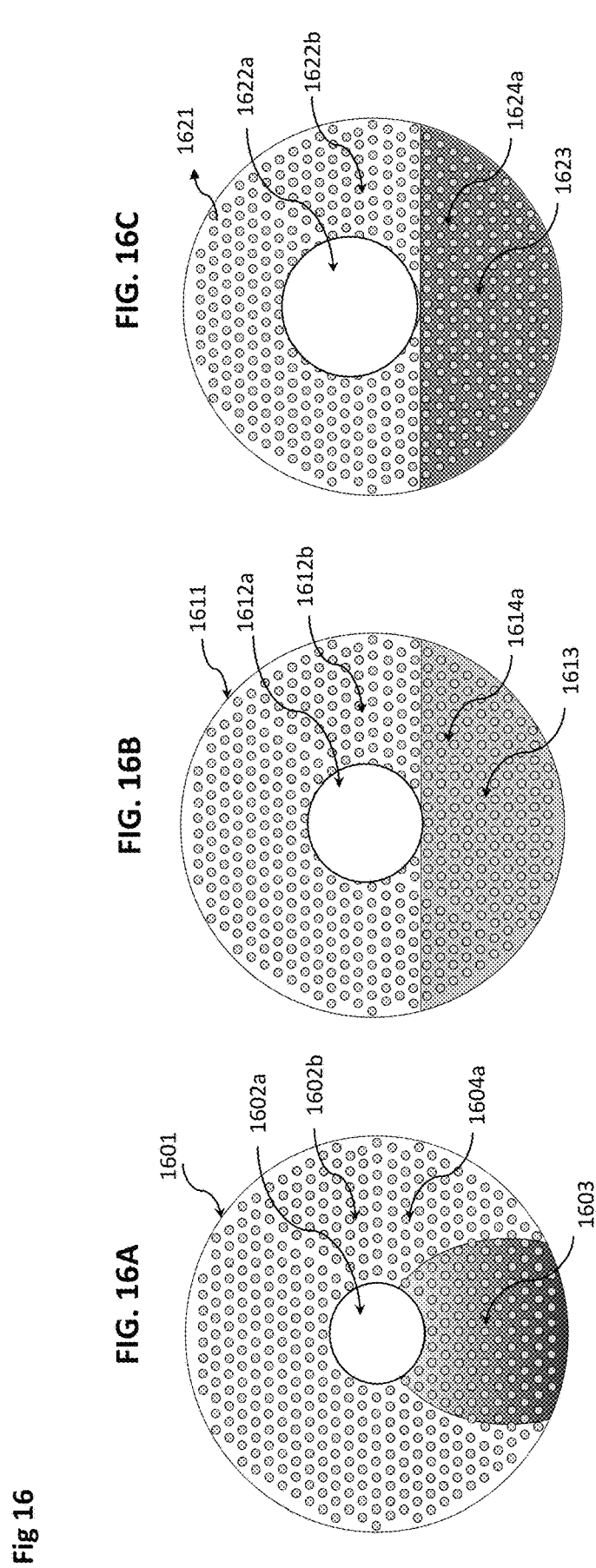
FIG. 16 is a schematic of an ophthalmic lens series with each ophthalmic lens comprising one or more first viewing regions, one or more second viewing regions and one or more myopia control elements for use in conjunction with Atropine or other pharmaceutical agent for myopia.

In some embodiments, a set or series or kit of ophthalmic lenses or ophthalmic lens designs for use in conjunction with atropine or atropine related compounds may be provided. The ophthalmic lenses in the series or set or kit may comprise fully finished or semi-finished blanks or lens surface manufacturing files for lens surfacing machines, for example, surface generators or CNC machines. The set or series or kit may consist of a plurality of ophthalmic lenses and/or lens designs, the ophthalmic lenses or lens designs comprising a feature configured, at least in part, based on the concentration of muscarinic receptor antagonist (e.g., Atropine or Atropine related compounds). FIG. 16 illustrates a series of ophthalmic lenses or ophthalmic lens designs configured to be used based on the concentration of the muscarinic receptor antagonist (e.g., Atropine or Atropine related compounds). As illustrated, the lenses in the series include at least one first viewing region (1602a, 1612a, 1622a) with at least one dimension (e.g., the size) of which may be selected based, at least in part, on the concentration of the muscarinic receptor antagonist (e.g., Atropine or Atropine related compounds). As illustrated, the size of the first viewing region is smaller (1602a) when used in conjunction with low concentrations of Atropine and is larger (1612a and 1622a) when used in conjunction with moderate and high concentrations of the muscarinic receptor antagonist (e.g., Atropine or Atropine related compound). In some embodiments, at least one of the first viewing regions 1602a, 1612 a and 1622a may incorporate a power profile to control, reduce and/or minimize one or more of higher order aberrations resulting from an increase in the pupillary diameter. Additionally, the lens may have at least one second viewing region (1603, 1613, 1623) that is placed about inferiorly to the first viewing region 1602a, 1612a and 1622a respectively and has a dioptric power profile that is more positive relative to the dioptric power in the first viewing region to enable substantially normal vision for near distances. The dimensions, i.e. size of the second viewing region and/or the relatively more positive power of the second viewing region may be selected based, at least in part, on the concentration of the muscarinic receptor antagonist (e.g., Atropine or Atropine related compound) to be used in conjunction with the ophthalmic lens. In some embodiments, each of the lenses or designs in the series or kit of lenses may have a relatively more positive power in the second viewing region relative to first viewing region and may be categorized as having one of the one or more second viewing regions with a low, medium, and/or high add powers. The lens 1601 may have a low add power in the second viewing region 1603 and may be associated with a smaller increase in the size of the first viewing region 1602a and may be used in conjunction with low concentrations of atropine (≤0.01% atropine). In some embodiments, the low add power in the second viewing region 1602a may be ≤+1.00D. The lens 16011 may have a moderate add power in the second viewing region 1613 and may be associated with a moderate increase in the size of the first viewing region 1612a and may be used in conjunction with moderate concentrations of the muscarinic receptor antagonist (e.g., Atropine or Atropine related compounds) (e.g., >0.01 to 0.1% atropine). In some embodiments, the moderate add power in the second viewing region may range from ≥+1.00D to ≤+2.00D or ≥+1.00D to ≤+2.50D. The lens 1621 may have a high add power in the second viewing region 1623 and may be associated with a large increase in the size of the first viewing region 1622*a* and may be used in conjunction with high concentrations of muscarinic receptor antagonist (e.g., Atropine or Atropine related compounds) (e.g., >0.10% atropine). In some embodiments, the high add power in the second viewing region may be ≥+1.50D to ≤+3.50D. Additionally, each of the lenses 1601, 1611 and 1621 in the series or kit or set of lenses or lens designs may have one or more myopia control elements (1604*a*, 1614*a* and 1624*a*) across the one or more viewing regions of the lenses or across the entire area of each of the lenses and may be configured based on the concentration of Atropine or Atropine based compounds. In some embodiments, as illustrated in FIG. 16C the lens 1621 may be designed for a higher concentration of atropine and may have myopia control elements 1624*a* in a second viewing region 1623 that may be different (e.g., smaller) and have a lower fill factor than the myopia control elements in a first viewing region 1622*b*.

Figure 17:
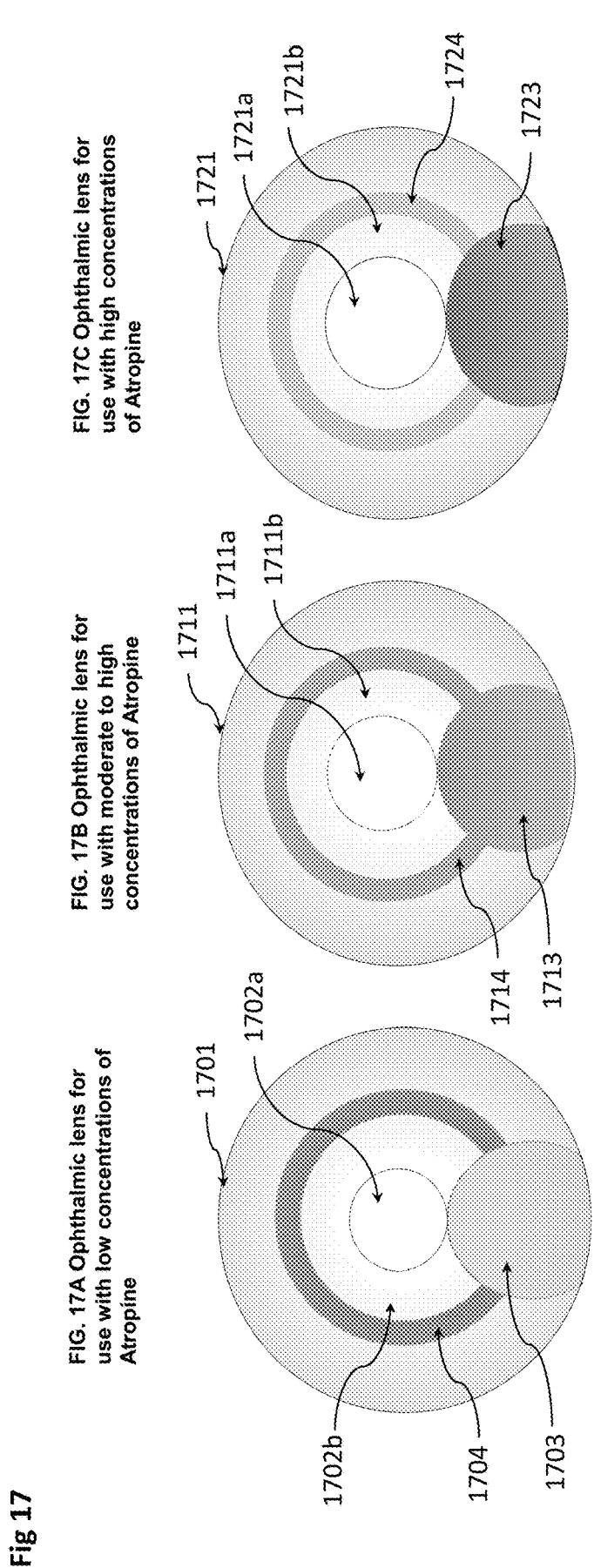
FIG. 17 is a schematic of an ophthalmic lens series with each ophthalmic lens comprising one or more first viewing regions, at least one second viewing regions and one or more myopia control elements and designed for use in conjunction with Atropine or other pharmaceutical agent for myopia.

FIG. 17 illustrates another set of ophthalmic lenses or ophthalmic lens designs configured to be used based on the concentration of the muscarinic receptor antagonist (e.g., Atropine or Atropine related compounds). As illustrated in FIGS. 17A to 17C, the lenses in the series include at least one or more first viewing regions (1702*a* to 1751*a* respectively) with at least one dimension (e.g., the size) of which may be selected based, at least in part, on the concentration of the muscarinic receptor antagonist (e.g., Atropine or Atropine related compounds). As illustrated, the size of one of the first viewing region 1702*a* is smaller when used in conjunction with low concentrations of Atropine and is larger (1711*a* and 1721*a*) when used in conjunction with moderate and high concentrations of the muscarinic receptor antagonist (e.g., Atropine or Atropine related compound). In some embodiments, at least one of the first viewing regions 1702*a*, 1711 *a* and 1721*a* may incorporate a power profile to control, reduce and/or minimize one or more of higher order aberrations resulting from an increase in the pupillary diameter. Additionally, the lens may have at least one second viewing region (1703 in lens 1701) that is placed about inferiorly to a first viewing region 1702*a* and has a dioptric power profile that is more positive relative to the dioptric power in the first viewing region to enable substantially normal vision for near distances. The dimensions, i.e., size of the second viewing region and/or the relatively more positive power may be selected based, at least in part, on the concentration of the muscarinic receptor antagonist (e.g., Atropine or Atropine related compound) to be used in conjunction with the ophthalmic lens. In some embodiments, the lenses in the series or kit of lenses may have a relatively more positive power in the second viewing region relative to a first viewing region and may be categorized as having a low or a medium or a high add power. A low add power in the second viewing region 1703 may be associated with a smaller increase in the size of the first viewing region and may be used in conjunction with low concentrations of atropine (≤0.01% atropine). A moderate add power in the second viewing region 1713 may be associated with a moderate increase in the size of the first viewing region and may be used in conjunction with moderate concentrations of the muscarinic receptor antagonist (e.g., Atropine or Atropine related compounds) (e.g., >0.01 to 0.1% atropine). A high add power in the second viewing region 1723 may be associated with a large increase in the size of the first viewing region and may be used in conjunction with high concentrations of muscarinic receptor antagonist (e.g., Atropine or Atropine related compounds) (e.g., >0.1% atropine). Additionally, in some embodiments, the strength or magnitude of the one or more myopia control elements (1704 to 1754) may be configured based on the concentration of Atropine or Atropine based compounds. In some embodiments, the strength or magnitude of one or more of the myopia control elements (1704) may be high when used in conjunction with low concentration of atropine to enhance the slowing of myopia. In some embodiments, the myopia control elements (1714 and 1724) may be of relatively lower strength or magnitude compared to 1704 when used in conjunction with higher concentrations of atropine.

In some embodiments, as illustrated in FIGS. 18A to 18C for the set of ophthalmic lenses or ophthalmic lens designs configured to be used based on the concentration of the muscarinic receptor antagonist (e.g., Atropine or Atropine related compounds), the area occupied by the one or more of the myopia control elements may be high (1834) when used in conjunction with low concentration atropine to enhance the stimulus to the eye to slow or reduce the progression of myopia. In some embodiments, the area occupied by the one or more of the myopia control elements be may low (1844 and 1854) when used in conjunction with moderate to high concentration atropine to reduce visual disturbances to the eye of the user.

In some embodiments, the ophthalmic lenses or lens series may be further tailored to comprise a photochromic filter or a light absorbing filter or a light absorbing element or a photo mask or a phase shift mask to minimize or reduce the visual disturbances. In some embodiments, the density or gradation or location across the lens of the photochromic filter or a light absorbing filter may be selected based upon the concentration of the muscarinic receptor antagonist (e.g., Atropine or Atropine related compounds) in use. In some embodiments, the density or gradation of light filtering elements may be lower or cover a lesser area of the lens for lower concentrations of the muscarinic receptor antagonist (e.g., Atropine or Atropine related compounds) and may be higher or greater for higher concentrations of the muscarinic receptor antagonist (e.g., Atropine or Atropine related compounds). In some embodiments, the density or light filtering elements or area coverage may be selected based on the size of the first viewing region and/or the relatively more positive power of the second viewing region. For example, in some embodiments, the density of the light filtering or photochromic filter may be about 25% or lower for small increase in the size of the first viewing region and/or relative positive power of ≤+1.00D. In some embodiments, the density of the light filtering or photochromic filter may be about 25% to 50% for moderate increase in the size of the first viewing region and/or relatively more positive power of +1.00 to +2.00D and may be about >50% for larger increases in the size of the first viewing region and/or relative positive power of >+2.00D.

One aspect of embodiments described herein provides a method of managing progression of myopia in an eye and includes; a) detection or identification of myopia and/or progression of myopia; b) determining the concentration of the pharmaceutical agent to be prescribed for use to slow, retard or control the progression of myopia and c) selecting one of the ophthalmic lenses from a series or a kit or a plurality of ophthalmic lenses based on the concentration of the pharmaceutical agent in use, wherein the ophthalmic lens comprises a base lens with a front and back surface and one or more myopia control elements, one or more first viewing regions with a first power profile selected to substantially correct for a distance refractive error of the eye, wherein the one or more features of at least one of the first viewing regions, such as the size is selected based, at least in part, on the concentration of the pharmaceutical agent and designed to minimize or reduce visual disturbances for the eye.

Another aspect of embodiments described herein provides a method of managing progression of myopia in an eye and includes; a) detection or identification of myopia and/or progression of myopia; b) determining the concentration of the pharmaceutical agent to be prescribed for use to slow, retard or control the progression of myopia and c) selecting one of the ophthalmic lenses from a series or a kit or a plurality of ophthalmic lenses based on the concentration of the pharmaceutical agent in use, wherein the ophthalmic lens comprises a base lens with a front and back surface, and one or more myopia control elements, and one or more first viewing regions with a first power profile selected to substantially correct for a distance refractive error of the eye, and one or more second viewing regions with a power profile that is relatively positive compared to the one or more first viewing regions, and wherein the one or more features of at least one of the first viewing regions, such as the size is selected based, at least in part, on the concentration of the pharmaceutical agent and designed to minimize or reduce visual disturbances for the eye and, wherein at least one or more features of the second viewing region such as the size and the relatively more positive power of the second viewing regions is selected based, at least in part, on the concentration of the pharmaceutical agent to compensate for the accommodative changes of the eye attributable to the pharmaceutical agent.

Figure 19B:
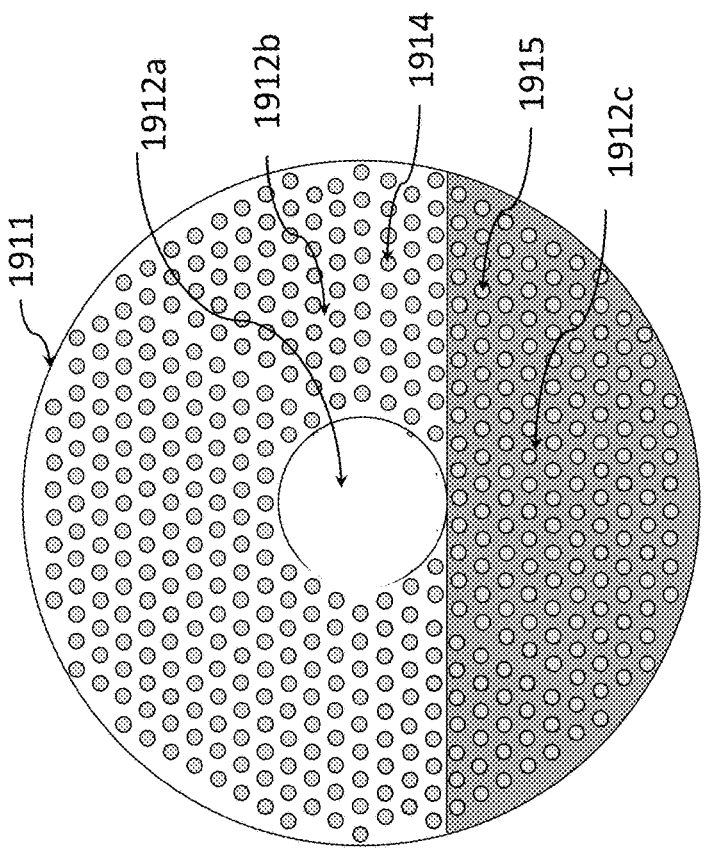
FIGS. 19A and 19B are schematics illustrating spectacle lenses 1901 and 1911 designed with one or more features selected, at least in part, based on the concentration of the muscarinic receptor antagonist (e.g., Atropine or Atropine related compounds)
Figure 19A:
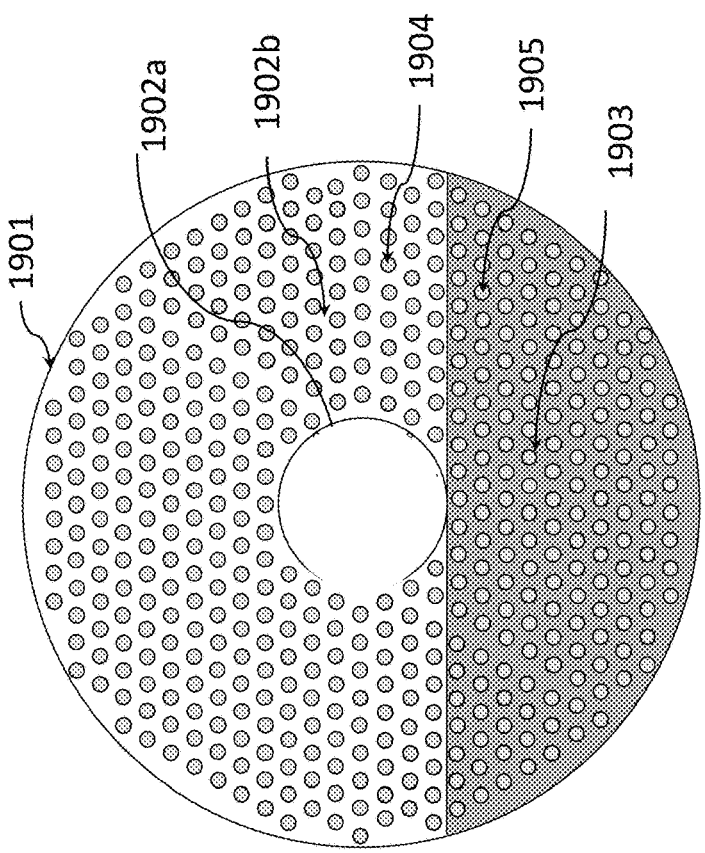

FIG. 19A is an illustration of a spectacle lens 1901 used in conjunction with a muscarinic receptor antagonist (e.g., Atropine or Atropine related compound) to slow myopia progression whilst minimizing, reducing and/or eliminating vision disturbances. The power profile of the first viewing regions 1902*a* and 1902*b* are configured to correct the distance refractive error. In FIG. 19A the dimensions of at least one of the first viewing regions 1902*a* and/or at least one of the second viewing regions 1903 are sized based, at least in part, on the concentration of the muscarinic receptor antagonist (e.g., Atropine or Atropine related compound) in use. Additionally, the dioptric power of the second viewing region 1903 is relatively more positive compared to the first viewing regions 1902*a* and 1902*b* to reduce and/or minimize visual disturbances when the individual is looking at near distances and is based, at least in part, on the concentration of the muscarinic receptor antagonist (e.g., Atropine or Atropine related compound) in use. Furthermore, the myopia control elements 1904 and 1905 are a plurality of refractive lenslets that are similarly sized and are distributed across the lens surface including in one of the first viewing regions 1902*b* and the second viewing region 1903. But there are no myopia control elements located in the centrally positioned first viewing region 1902*a*.

FIG. 19B is an illustration of a spectacle lens 1911 used in conjunction with a muscarinic receptor antagonist (e.g., Atropine or Atropine related compound) to slow myopia progression whilst minimizing, reducing and/or eliminating vision disturbances. The lens 1911 has 3 first viewing regions 1912*a*, 1912*b* and 1912*c* configured with a power profile to correct the distance refractive error and the dimensions of at least one of the first viewing regions are sized based, at least in part, on the concentration of the muscarinic receptor antagonist (e.g., Atropine or Atropine related compound) in use. Unlike FIG. 19A, the lens 1911 does not include a second viewing region that has a different power profile to the at least one of the first viewing regions. The myopia control elements 1914 and 1915 are similarly sized and are distributed across the lens surface including the first viewing regions 1912*b* and 1912*c*. But there are no myopia control elements positioned in the first (central located) viewing region 1912*a*. The power profile of the myopia control elements 1914 and 1915 are also selected based, at least in part, on the concentration of the muscarinic receptor antagonist (e.g., Atropine or Atropine related compound) in use. The myopia control elements 1915 in shaded region 1912*c* have a relatively more positive power profile compared to the myopia control elements 1914 in region 1912*b* to reduce and/or minimize the stronger myopia progression stimuli arising when the individual is looking at near distances and is based, at least in part, on the concentration of the muscarinic receptor antagonist (e.g., Atropine or Atropine related compound) in use.

FIG. 19C provides a list of example ophthalmic lenses and their lens power profile parameters selected for 5 progressing myopes prescribed 0.05% Atropine to control their myopia and selected based at least, in part, on the concentration of the pharmaceutical agent in use to reduce and/or minimize visual disturbances and/or accommodative changes. Each of the 5 myopes using the an example ophthalmic lens shown in FIG. 19C have an identical power profile requirement in each eye and a similar myopia progression history in each eye and are therefore fitted with ophthalmic lenses of identical parameters in each eye. However, in some other examples, the at least one or more parameters of the ophthalmic lenses selected based at least in part the concentration of the pharmaceutical agent in use to, for example, reduce and/or minimize visual disturbances or accommodative changes may not be equal in each eye or may be powered and/or positioned differently between eyes. Example lenses 1 to 4 in FIG. 19C relate to the ophthalmic lens configuration 1901 illustrated in FIG. 19A and includes at least one second viewing region relatively more positive in power profile compared to at least one of the first viewing regions 1902*a* and 1902*b* to reduce and/or minimize visual disturbances when the individual is looking at near distances and is based, at least in part, on the concentration of the muscarinic receptor antagonist (e.g., Atropine or Atropine related compound) in use. Examples lens 5 relates to the ophthalmic lens configuration 1911 illustrated in FIG. 19B and may not contain a second viewing region. All example lenses provide a power profile in at least one of the first viewing regions to correct the spherical refractive error of the myope except for the lens of example 4 which provides a sphero-cylindrical refractive error correction. Example lenses 1, 2, 4 and 5 also incorporate myopia control elements having a power profile that provide a relatively more positive power than the first power profile of the at least one first viewing region and, as such, provide a myopic defocus, i.e. a focus in front of the retinal plane. The lens of example 3 incorporates myopia control elements having a power profile that are relatively more negative power (−3.00D) than the at least one first power profile of at least one of the first viewing regions and, as such, provide a hyperopic defocus, i.e. a focus behind the retinal plane. The resultant net power profile of the relatively more negative (−3.00D) myopia control elements 1914 than a first power profile of a first viewing region 1912*b* is −8.00D (−5.00D base power profile to correct for the distance refractive error plus −3.00D power profile of the hyperopic defocus lenslet 1914). However, in the second viewing region 1903 the resultant net power profile of the relatively more negative (−3.00D) myopia control element 1905 than the first power profile is −6.00D (−5.00D base power profile to correct for the distance refractive error plus +2.00D additional power included in a second viewing region 1903 plus −3.00D power profile of the hyperopic defocus lenslets 1815). In this lens of example 5 based on the configuration of lens 1911 illustrated in FIG. 19B and the lens parameters of example 5 shown in FIG. 19C, the power profile of the first viewing regions 1912*a-c* provided to correct the distance refractive error of the progressing myope is −2.00D. The myopia control elements 1914 distributed across a first viewing region 1912*b* may have a lesser strength e.g., power profile (+1.50D) in comparison to the myopia control elements 1915 (+3.50D) distributed across one of the first viewing (shaded) regions 1912*c* to ensure that adequate myopia control may be provided during near tasks, as excessive near tasks are considered to exacerbate myopia.

Examples

A1. An ophthalmic lens for use in conjunction with a pharmaceutical agent for an eye of an individual with myopia comprising: a base lens with a front and back surface and a first power profile to correct for a distance refractive error of the eye; one or more myopia control elements on one or more surfaces; one or more first viewing regions, wherein the size of at least one of the first viewing region is selected based, at least in part, on the concentration of the pharmaceutical agent to compensate for a change in pupillary diameter attributable to the pharmaceutical agent.

A2. An ophthalmic lens for use in conjunction with a pharmaceutical agent for an eye of an individual with myopia comprising: a base lens with a front and back surface and a first power profile to correct for a distance refractive error of the eye; one or more myopia control elements on one or more surfaces; one or more first viewing regions, wherein the size of at least one of the first viewing region is selected based, at least in part, on the concentration of the pharmaceutical agent to compensate for a change in pupillary diameter attributable to the pharmaceutical agent and one or more second viewing regions, at least one of the second viewing regions comprising a power profile that is relatively more positive compared to the first viewing region, wherein at least one of the size and the relatively more positive power of the second viewing regions is selected based, at least in part, on the concentration of the pharmaceutical agent to compensate for the accommodative changes of the eye attributable to the pharmaceutical agent.

A3. An ophthalmic lens for treating myopia comprising: a base lens with a front surface, a back surface, and a first power profile selected to correct or substantially correct for a distance refractive error of the eye; one or more myopia control elements on at least one of the front and back surfaces of the lens; a first viewing region having is size selected based, at least in part, on a concentration of a pharmaceutical agent for use in conjunction with ophthalmic lens, the first viewing region being configured to minimize, reduce and/or eliminate vision disturbances for distance vision; and a second viewing region comprising a power profile that is relatively more positive compared to the first viewing region; wherein at least one of the size of the second viewing region and the relatively more positive power of the second viewing region is selected based, at least in part, on the concentration of the pharmaceutical agent.

A4. The ophthalmic lens of example A2, wherein the size of the first viewing region is selected based, at least in part, on a concentration of a pharmaceutical agent to compensate for a change in pupillary diameter attributable to the pharmaceutical agent.

A5. The ophthalmic lens of example A2, A3, or A4, wherein the at least one of the size of the second viewing region and the relatively more positive power of the second viewing region is selected based, at least in part, on a concentration of a pharmaceutical agent to compensate for the accommodative changes of the eye attributable to the pharmaceutical agent.

A6. The ophthalmic lens of any of the A examples, wherein the pharmaceutical agent is a muscarinic receptor antagonist.

A7. The ophthalmic lens of any of the A examples, wherein the pharmaceutical agent is Atropine, or an Atropine based compound.

A8. The ophthalmic lens of any of the A examples, wherein the one or more myopia control elements may be disposed across the entire lens or may be disposed in one or more regions of the lens.

A9. The ophthalmic lens of any of the A examples, wherein the second viewing region is positioned at any combination of one or more of inferior, superior, temporal, nasal, oblique, concentric co-axial, concentric non co-axial, eccentric, non-concentric, inferonasal, inferotemporal or any other position relative to the at least one first viewing region.

A10. The ophthalmic lens of any of the A examples, wherein the ophthalmic lens further comprises a light absorbing filter or a light absorbing element or a photochromic filter to further reduce, minimize or eliminate visual disturbance for the eye, and wherein the color and/or intensity of the light absorbing element, or a photochromic filter is based, at least in part, on the concentration of the pharmaceutical agent.

A11. The ophthalmic lens of any of the A examples, wherein the one or more myopia control elements is refractive, diffractive, contrast modulating, phase-modulating, meta-surfaces, light scattering, aberrated, holographic, diffusing, or a combination of one or more elements thereof.

A12. The ophthalmic lens of any of the A examples, wherein the one or more myopia control elements are present across one or both surfaces of the ophthalmic lens and is present across the entire surface or limited to one or more regions of the lens.

A13. The ophthalmic lens of any of the A examples, wherein factors including any combination of one or more of size, arrangement and fill factor of the myopia control elements in the respective viewing regions may vary with respect to each other.

A14. The ophthalmic lens of any of the A examples, wherein the one or more myopia control elements are a discrete element, an element incorporated in the power profile of the ophthalmic lens or a combination of both.

A15. The ophthalmic lens of any of the A examples, wherein the one or more myopia control elements are refractive elements and is a lenslet or may be a variation of the power profile of the lens that provides myopic defocus, hyperopic defocus, or an extended depth of focus.

A16. The ophthalmic lens of any of the A examples, wherein the one or more myopia control elements are refractive and have a relatively more positive power, relatively more negative power, or a combination of both compared to the rest of the lens power profile.

A17. The ophthalmic lens of any of the A examples, wherein the arrangement, size, magnitude and/or strength of the one or more refractive, meta-surfaces, diffractive, contrast modulating, light scattering, aberrated, holographic, diffusing, and/or phase modulating myopia control elements or a combination of one or more of the elements is varied across the regions of the ophthalmic lens based, at least in part, on the rate of myopia progression of the eye of the individual.

A18. The ophthalmic lens of any of the A examples, wherein the dimension, arrangement, location, type and/or fill factor of the one or more myopia control elements is configured based, at least in part, on the concentration of the pharmaceutical agent.

A19. The ophthalmic lens of any of the A examples, wherein the size (or dimension) of the first viewing region is determined at least in part on the equation: Distance viewing region size for normal non-atropine wearer+6.924+0.6266*LN (Concentration of Atropine %/100).

A20. The ophthalmic lens of any of the A examples, wherein the size of the first viewing region to be used in conjunction with the pharmaceutical agent is about 4% to about 95% (e.g., about 5%, 10%, 15%, 20%, 25%, 30%, 35%, 40%, 45%, 50%, 55%, 60%, 65%, 70%, 75%, 80%, 85%, 90%, or 95%) larger compared to the size of the first viewing region without the use of the pharmaceutical agent.

A21. The ophthalmic lens of any of the A examples, wherein the relative positive power in the second viewing region with pharmaceutical agent concentrations of 0.01% or lower is about ≤1.00D.

A22. The ophthalmic lens of any of the A examples, wherein the relative positive power in the second viewing region with pharmaceutical agent concentrations ranging from 0.02% to 0.1% is about ≥+1.00D to ≤+2.00D.

A23. The ophthalmic lens of any of the A examples, wherein the relative positive power in the second viewing region with pharmaceutical agent concentrations greater than 0.1%, is about ≥+1.50D or higher.

A24. The ophthalmic lens of any of the A examples, wherein the size of the second viewing region (704a) increases as the concentrations of the pharmaceutical agent increases.

A25. The ophthalmic lens of any of the A examples, wherein the one or more myopia control elements are present on about 90% or more of the lens surface, about 85% of lens surface, about 80% of lens surface, about 75% of lens surface, about 70% of lens surface, about 65% of the lens surface, about 60% of lens surface, about 55% of lens surface, about 50% of lens surface, about 45% of lens surface, about 40% of the lens surface, about 35% of the lens surface, about 30% of the lens surface and about 25% of the lens surface.

A26. The ophthalmic lens of any of the A examples, wherein the ophthalmic lens is a spectacle lens (including e.g., a clip on spectacle lens, or a stick on film) or a contact lens.

A27. A set of lenses or series of lens designs for ophthalmic lenses to be used in conjunction with a pharmaceutical agent for slowing the progression of myopia, the set of lenses or series of lens designs comprising a plurality of lenses as defined in any of the A examples, wherein the features of the plurality of lenses are selected to be used based, at least in part, on the concentration of the pharmaceutical agent to be used.

B1. An ophthalmic lens for use in conjunction with a pharmaceutical agent for an eye with myopia, the ophthalmic lens comprising: a base lens with a front surface and a back surface; at least one first viewing region having a first power profile, wherein the size of the at least one first viewing region is configured based, at least in part, on the concentration of the pharmaceutical agent; and one or more myopia control elements with a power profile different than the first power profile.

B2. The ophthalmic lens of example B1, wherein the first power profile is selected to correct or substantially correct for a refractive error (e.g., a distance refractive error) of the eye.

B3. The ophthalmic lens of any of examples B1 or B2, wherein the size of at least one of the first viewing regions is selected based, at least in part, on the concentration of the pharmaceutical agent to reduce or minimize vision disturbances that may result from the change in pupillary diameter attributable to the pharmaceutical agent.

B4. The ophthalmic lens of any of the B examples, wherein the power profile of at least one of the first viewing regions is selected based, at least in part, on the concentration of the pharmaceutical agent to reduce one or more of a third order aberration, fourth order aberration, fifth order aberration, sixth order aberration, one or more of other higher order aberrations or a combination of one or more thereof to minimize vision disturbances that may result from the change in pupillary diameter attributable to the pharmaceutical agent.

B5. The ophthalmic lens of any of the B examples, wherein the at least one first viewing region is substantially aligned with one or more of the axes of the eye.

B6. The ophthalmic lens of any of the B examples, wherein the size of the at least one first viewing region is determined at least in part on the equation: One of the first viewing region size for normal non-atropine wearer+6.924+0.6266*LN (Concentration of Atropine %/100).

B7. The ophthalmic lens of any of the B examples, wherein the size of the at least one first viewing region is configured based on one of the 95% confidence interval, 97% confidence interval or the 99% confidence interval of the equation: One of the first viewing region size for normal non-atropine wearer+6.924+0.6266*LN (Concentration of Atropine %/100).

B8. The ophthalmic lens of any of the B examples, wherein the size of the at least one first viewing region is configured based on the size of the first viewing region without the use of the pharmaceutical agent and a percentage of the value estimated from the equation: "6.924+0.6266*LN (Concentration of Atropine %/100)".

B9. The ophthalmic lens of any of the B examples, wherein the size of the at least one first viewing region is configured based on the size of the first viewing region without the use of the pharmaceutical agent and a percentage of the value estimated from the equation: "6.924+0.6266*LN (Concentration of Atropine %/100)" and the percentage is from about 15% to about 85% (e.g., 15%, 20%, 25%, 30%, 35%, 40%, 45%, 50%, 55%, 60%, 65%, 70%, 75%, 80%, or 85%).

B10. The ophthalmic lens of any of the B examples, wherein the size of the at least one first viewing region to be used in conjunction with the pharmaceutical agent is about 4% to about 400% (e.g., about 5%, 10%, 15%, 20%, 25%, 30%, 35%, 40%, 45%, 50%, 55%, 60%, 65%, 70%, 75%, 80%, 85%, 90%, 95%, 100%, 110% 120%, 130%, 140%, 150%, 160%, 170%, 180%, 190%, 200%, 210%, 220%, 230%, 240%, 250%, 260%, 270%, 280%, 290% 300%, 310%, 320%, 330%, 340%, 350%, 360%, 370%, 380%, 390%, or 400%) larger compared to the size of the first viewing region without the use of the pharmaceutical agent.

B11. The ophthalmic lens of any of the B examples, wherein the position, arrangement, tint, power profile, and presence of myopia control elements of at least one of the first viewing regions is configured based, at least in part, on the concentration of the pharmaceutical agent.

B12. The ophthalmic lens of any of the B examples, further comprising at least one second viewing region with a second power profile different than the first power profile.

B13. The ophthalmic lens of example B12, wherein the second power profile is at least one of relatively more positive in power than the first power profile or relatively more negative than the first power profile.

B14. The ophthalmic lens of any of examples B12 or B13, wherein the second power profile is relatively more positive in power than the first power profile and selected based, at least in part, on the concentration of the pharmaceutical agent.

B15. The ophthalmic lens of any of examples B12-B14, wherein the size of the at least one second viewing region is selected based, at least in part, on the concentration of the pharmaceutical agent.

B16. The ophthalmic lens of any of examples B12-B15, wherein a size of the at least one second viewing region varies with varying concentrations of the pharmaceutical agent.

B17. The ophthalmic lens of any of examples B12-B16, wherein a size of the at least one second viewing region increases with increasing concentrations of the pharmaceutical agent.

B18. The ophthalmic lens of any of examples B13-B17, wherein at least one of the second power profile and the size of the at least one second viewing region is selected based, at least in part, on the concentration of the pharmaceutical agent.

B19. The ophthalmic lens of any of examples B12-B18, wherein the size of the at least one second viewing region is selected based, at least in part, on one or more of a loss of accommodation and/or to reduce or minimize visual disturbances (e.g., blur or visual discomfort from loss of accommodation).

B20. The ophthalmic lens of any of examples B12-B19, wherein the at least one second viewing region is positioned at any combination of one or more of inferior, superior, temporal, nasal, oblique, concentric co-axial, concentric non co-axial, eccentric, non-concentric, inferonasal, inferotemporal or any other position relative to the at least one first viewing region.

B21. The ophthalmic lens of any of examples B12-B20, wherein the second power profile (e.g., the relatively more positive power profile) in the at least one second viewing region ranges from about ≥+0.50D to about ≤+3.50D or about ≥+0.25D to about ≤+4.00D or about ≥+0.25D to about ≤+5.00D (e.g., the mean or effective power in the zone).

B22. The ophthalmic lens of any of examples B12-B21, wherein the second power profile (e.g., the relatively more positive power profile) in the at least one second viewing region with pharmaceutical agent concentrations of 0.01% or lower is about ≤1.00D.

B23. The ophthalmic lens of any of examples B12-B22, wherein the second power profile (e.g., the relatively more positive power profile) in the at least one second viewing region with pharmaceutical agent concentrations ranging from 0.02% to 0.1% is about ≥1.0D to ≤2.5D or about ≥1.0D to ≤3.0D.

B24. The ophthalmic lens of any of examples B12-B23, wherein the second power profile (e.g., the relatively more positive power profile) in the at least one second viewing region with pharmaceutical agent concentrations greater than 0.1%, is about ≥1.5D or higher or about ≥0.75D or higher or about ≥1.0D or higher.

B25. The ophthalmic lens of any of the B examples, wherein the power profile of any combination of one or more of the at least one first viewing region and at least one second viewing region is symmetric or asymmetric.

B26. The ophthalmic lens of any of the B examples, wherein any combination of the first power profile and the second power profile is rotationally symmetric or rotationally asymmetric.

B27. The ophthalmic lens of any of the B examples, wherein the ophthalmic lens further comprises any combination of one or more of a light absorbing filter, a light absorbing element, a photochromic filter, a photo mask, and a phase shift mask in one or more regions of the lens and is configured based, at least in part, on the concentration of the pharmaceutical agent.

B28. The ophthalmic lens of any of the B examples, wherein the power profile of the one or more myopia control elements is at least one of relatively more positive than one of the first power profiles or relatively more negative than one of the first power profiles.

B29. The ophthalmic lens of any of the B examples, wherein the power profile of the one or more myopia control elements is at least one of relatively more positive than one of the second power profiles or relatively more negative than one of the second power profiles.

B30. The ophthalmic lens of any of the B examples, wherein the power profile of the one or more myopia control elements is relatively more positive than the first power profile.

B31. The ophthalmic lens of any of the B examples, wherein the one or more myopia control elements are located on any combination of one or more of the front surface of the base lens the back surface of the base lens or in a bulk of the base lens.

B32. The ophthalmic lens of any of the B examples, wherein the combination of one or more of the shape, pattern, position and power profile of the one or more myopia control elements relative to the at least one first viewing region is selected based, at least in part, on the concentration of the pharmaceutical agent.

B33. The ophthalmic lens of any of the B examples, wherein the one or more myopia control elements are disposed across the entire lens or may be disposed in one or more regions of the lens.

B34. The ophthalmic lens of any of the B examples, wherein the one or more myopia control elements are present across one or both surfaces of the ophthalmic lens and is present across the entire surface or limited to one or more regions of the lens.

B35. The ophthalmic lens of any of the B examples, wherein the one or more myopia control elements are present in any combination of one or more of the at least one first viewing region and the at least one second viewing region.

B36. The ophthalmic lens of any of the B examples, wherein at least one of the at least one first viewing region and the at least one second viewing region are free of the myopia control elements.

B37. The ophthalmic lens of any of the B examples, wherein the at least one first viewing region is substantially devoid of myopia control elements.

B38. The ophthalmic lens of any of the B examples, wherein any combination of one or more of arrangement, type, size, magnitude, strength, location, and/or fill factor of the myopia control elements in the respective viewing regions may vary with respect to each other.

B39. The ophthalmic lens of any of the B examples, wherein the one or more myopia control elements are any combination of one or more of discrete elements, conjoined elements, continuous elements, discontinuous elements and an element incorporated in the power profile of the ophthalmic lens.

B40. The ophthalmic lens of any of the B examples, wherein the one or more myopia control elements comprise a power profile that provides myopic defocus, hyperopic defocus, no defocus or an extended depth of focus or a combination thereof.

B41. The ophthalmic lens of any of the B examples, wherein the one or more myopia control elements are a plurality of lenslets, one or more rings, opaque elements, non-refractive elements, defocus elements, or a plurality of discrete elements and may be a variation of the power profile of the lens that provides any combination of one or more of myopic defocus, hyperopic defocus, no defocus, or an extended depth of focus.

B42. The ophthalmic lens of any of the B examples, wherein the one or more myopia control elements are refractive and have a relatively more positive power, relatively more negative power or a combination of both compared to the first power profile.

B43. The ophthalmic lens of any of the B examples, wherein the one or more myopia control elements are refractive and have a relatively more positive power, relatively more negative power or a combination of both compared to the second power profile.

B44. The ophthalmic lens of any of the B examples, wherein the one or more myopia control elements are any combination of one or more of refractive, meta-surfaces, diffractive, contrast modulating, light scattering, aberrated, holographic, light diffusing, light deviating, light amplitude modulating and/or phase modulating.

B45. The ophthalmic lens of any of the B examples, wherein the arrangement, type, size, magnitude, strength, location, and/or fill factor of the one or more myopia control elements or a combination of one or more of the elements is varied across the regions of the ophthalmic lens based, at least in part, on the rate of myopia progression of the eye of the individual.

B46. The ophthalmic lens of any of the B examples, wherein the arrangement, type, size, magnitude, strength, location, and/or fill factor of the one or more myopia control elements is configured based, at least in part, on the concentration of the pharmaceutical agent.

B47. The ophthalmic lens of any of the B examples, wherein the one or more myopia control elements are present on about 90% or more of the base lens, about 85% of the base lens, about 80% of the base lens, about 75% of the base lens, about 70% of the base lens, about 65% of the base lens, about 60% of the base lens, about 55% of the base lens, about 50% of the base lens, about 45% of the base lens, about 40% of the base lens, about 35% of the base lens, about 30% of the base lens, about 25% of the base lens, about 20% of the base lens, about 15% of the base lens, or about 10% of the base lens.

B48. The ophthalmic lens of any of the B examples, wherein the one or more myopia control elements are present on about 90% or more of the at least one first viewing region, about 85% of the at least one first viewing region, about 80% of the at least one first viewing region, about 75% of the at least one first viewing region, about 70% of the at least one first viewing region, about 65% of the at least one first viewing region, about 60% of the at least one first viewing region, about 55% of the at least one first viewing region, about 50% of the at least one first viewing region, about 45% of the at least one first viewing region, about 40% of the at least one first viewing region, about 35% of the at least one first viewing region, about 30% of the at least one first viewing region, about 25% of the at least one first viewing region, about 20% of the at least one first viewing region, about 15% of the at least one first viewing region, or about 10% of the at least one first viewing region.

B49. The ophthalmic lens of any of the B examples, wherein the one or more myopia control elements are present on about 90% or more of the at least one second viewing region, about 85% of the at least one second viewing region, about 80% of the at least one second viewing region, about 75% of the at least one second viewing region, about 70% of the at least one second viewing region, about 65% of the at least one second viewing region, about 60% of the at least one second viewing region, about 55% of the at least one second viewing region, about 50% of the at least one second viewing region, about 45% of the at least one second viewing region, about 40% of the at least one second viewing region, about 35% of the at least one second viewing region, about 30% of the at least one second viewing region, about 25% of the at least one second viewing region, about 20% of the at least one second viewing region, about 15% of the at least one second viewing region, or about 10% of the at least one second viewing region.

B50. The ophthalmic lens of any of the B examples, wherein the one or more myopia control elements is refractive, non-refractive, diffractive, contrast modulating, phase-modulating, meta-surfaces, light scattering, aberrated, holographic, diffusing, light deviating, light amplitude modulating or a combination of one or more elements thereof.

B51. The ophthalmic lens of any of the B examples, wherein the shape, position and/or power profile of the one or more myopia control elements relative to the at least one first viewing region is selected based, at least in part, such that a rotational asymmetry of power profile (in at least one of the first viewing region and the second viewing region) is created by the one or more myopia control elements (e.g., a rotational asymmetry of strength of the one or more myopia control elements).

B52. The ophthalmic lens of any of the B examples, wherein the strength of the one or more myopia control elements decreases with increasing concentration of the pharmaceutical agent.

B53. The ophthalmic lens of any of the B examples, wherein the ophthalmic lens is a spectacle lens (including e.g., a clip on spectacle lens, or a stick on film) or a contact lens.

B54. The ophthalmic lens of any of the B examples, wherein the ophthalmic lens is a sphero-cylindrical lens, a toric lens, a multifocal lens, a bifocal lens, or a progressive addition lens.

B55. The ophthalmic lens of any of the B examples, wherein the pharmaceutical agent is a muscarinic receptor antagonist.

B56. The ophthalmic lens of any of the B examples, wherein the pharmaceutical agent is Atropine or Atropine related compound.

B57. A set of lenses or series of lens designs for ophthalmic lenses to be used in conjunction with a pharmaceutical agent for slowing the progression of myopia, the set of lenses or series of lens designs comprising a plurality of lenses as defined in any of the B examples, wherein the features of the plurality of lenses are selected to be used based, at least in part, on the concentration of the pharmaceutical agent to be used.

C1. An ophthalmic lens series for use in conjunction with a pharmaceutical agent for an eye with myopia, the lenses in the series comprising: a base lens with a front and back surface and one or more myopia control elements; at least one first viewing region with a first power profile selected to correct for a refractive error (e.g., distance refractive error) of the eye and to substantially control, minimize, and/or reduce one or more of the higher order aberrations of the eye.

C2. The ophthalmic lens series of example C1, wherein the lenses in the series comprise one or more features of the ophthalmic lenses of examples B1-B57.

D1. An ophthalmic lens series for use in conjunction with a pharmaceutical agent for an eye with myopia, the lenses in the series comprising: a base lens with a front and back surface and one or more myopia control elements; at least one first viewing region with a first power profile selected to correct for a refractive error (e.g., distance refractive error) of the eye and to substantially control, minimize, and/or reduce one or more of the higher order aberrations of the eye, and wherein the size of the at least one first viewing region is configured based, at least in part, on the concentration of the pharmaceutical agent.

D2. The ophthalmic lens series of example D1, wherein the lenses in the series comprise one or more features of the ophthalmic lenses of examples B1-B57.

E1. An ophthalmic lens series for use in conjunction with a pharmaceutical agent for an eye with myopia, the lenses in the series comprising: a base lens with a front and back surface and one or more myopia control elements; at least one first viewing region with a first power profile selected to substantially correct for a refractive error (e.g., distance refractive error) of the eye, wherein the size of the at least one first viewing region is configured based, at least in part, on the concentration of the pharmaceutical agent.

E2. The ophthalmic lens series of example E1, wherein the size of the at least one first viewing region of the lenses in the series is configured based on one of the 95% confidence interval, 97% confidence interval or the 99% confidence interval of the equation: One of the first viewing region size for normal non-atropine wearer+6.924+0.6266*LN (Concentration of Atropine %/100).

E3. The ophthalmic lens series of any of examples E1 and E2, wherein the lenses in the series further comprise at least one second viewing region with at least one power profile that is relatively more positive than the one or more first viewing regions and selected based, at least in part, on the concentration of the pharmaceutical agent and the relatively more positive power ranges from about ≥+0.50D to about ≤+3.50D or about ≥+0.25D to about ≤+4.00D or about ≥+0.25D to about ≤+5.00D (e.g., the mean or effective power in the zone).

E4. The ophthalmic lens series of any of examples E1-E3, wherein the lenses in the series comprise one or more features of the ophthalmic lenses of examples B1-B57.

F1. An ophthalmic lens series for use in conjunction with a pharmaceutical agent for an eye with myopia, the lenses of the series comprising: a base lens with a front and back surface and one or more myopia control elements interspersed on and/or in the lens; at least one first viewing region with a first power profile selected to substantially correct for a refractive error (e.g., distance refractive error) of the eye, wherein the size of at least one of the first viewing regions is configured based, at least in part, on the concentration of the pharmaceutical agent; and at least one second viewing region with a second power profile that is different (e.g., relatively more positive or negative) than the at least one first viewing region and selected based, at least in part, on the concentration of the pharmaceutical agent and the different power ranges from about ≥+0.50D to about ≤+3.50D.

F2. The ophthalmic lens series of example F1, wherein the lenses in the series comprise one or more features of the ophthalmic lenses of examples B1-B57.

G1. An ophthalmic lens series for use in conjunction with a pharmaceutical agent for an eye with myopia, the lenses of the series comprising: a base lens with a front and back surface and one or more myopia control elements interspersed on and/or in the lens; at least one first viewing region with a first power profile selected to substantially correct for a refractive error (e.g., distance refractive error) of the eye, wherein the size of at least one first viewing region is configured based, at least in part, on the concentration of the pharmaceutical agent; at least one second viewing region with a second power profile that is different (e.g., relatively more positive or negative) than the at least one first viewing region and selected based, at least in part, on the concentration of the pharmaceutical agent and the different power ranges from about ≥+0.50D to about ≤+3.50D; and a light absorbing filter or a light absorbing element or a photochromic filter or a photo mask or a phase shift mask in one or more regions of the lens and configured based, at least in part, on the concentration of the pharmaceutical agent.

G2. The ophthalmic lens series of example G1, wherein the lenses in the series comprise one or more features of the ophthalmic lenses of examples B1-B57.

H1. A spectacle lens series for use in conjunction with a pharmaceutical agent for an eye with myopia, the lenses in the series comprising: a base lens with a front and back surface and one or more myopia control elements interspersed on and/or in the lens; at least one first viewing region with a first power profile selected to substantially correct for a refractive error (e.g., distance refractive error) of the eye, wherein the size of at least one first viewing region is configured based, at least in part, on the concentration of the pharmaceutical agent; at least one second viewing region with a second power profile that is relatively more positive than the at least one first viewing region from about ≥+0.50D to about ≤+3.50D, and selected based, at least in part, on the concentration of the pharmaceutical agent in use, and positioned at any combination of one or more of central, peripheral, inferior, superior, temporal, nasal, oblique, concentric co-axial, concentric non co-axial, eccentric, non-concentric, inferonasal, inferotemporal or any other position relative to the at least one first viewing region.

H2. The spectacle lens series of example H1, wherein the lenses in the series further comprise a light absorbing filter or a light absorbing element or a photochromic filter or a photo mask or a phase shift mask in one or more regions of the lens and is configured based, at least in part, on the concentration of the pharmaceutical agent.

H3. The ophthalmic lens series of example H1, wherein the lenses in the series comprise one or more features of the ophthalmic lenses of examples B1-B57.

I1. A contact lens series for use in conjunction with a pharmaceutical agent for an eye with myopia, the lenses in the series comprising: a base lens with a front and back surface and one or more myopia control elements interspersed on and/or in the lens; at least one first viewing region with a first power profile selected to substantially correct for a refractive error (e.g., distance refractive error) of the eye, wherein the size of at least one first viewing region is configured based, at least in part, on the concentration of the pharmaceutical agent; at least one second viewing region with a second power profile that is different (e.g., relatively more positive) than the at least one first viewing region from about ≥+0.50D to about ≤+3.50D, and selected based, at least in part, on the concentration of the pharmaceutical agent in use, and positioned at any combination of one or more of inferior, superior, temporal, nasal, oblique, concentric co-axial, concentric non co-axial, eccentric, non-concentric, inferonasal, inferotemporal or any other position relative to the at least one first viewing region.

I2. The contact lens series of example I1, wherein the lenses in the series further comprise a light absorbing filter or a light absorbing element or a photochromic filter or a photo mask or a phase shift mask in one or more regions of the lens and is based, at least in part, on the concentration of the pharmaceutical agent.

I3. The ophthalmic lens series of example I1, wherein the lenses in series comprise one or more features of the ophthalmic lenses of examples B1-B57.

J1. A method of managing progression of myopia in an eye, comprising: detecting (or identifying) myopia and/or progression of myopia in an eye; determining the concentration of the pharmaceutical agent to be prescribed for use to slow, retard or control the progression of myopia; and selecting an ophthalmic lens from a series or a kit or a plurality of ophthalmic lenses based on the concentration of the pharmaceutical agent in use; wherein the ophthalmic lens comprises: a base lens with a front and back surface, and one or more myopia control elements, at least one first viewing region with a first power profile selected to substantially correct for a refractive error (e.g., a distance refractive error) of the eye; and at least one second viewing region with a second power profile that is different (e.g., relatively positive or negative) compared to the first power profile, and wherein one or more features of at least one of the first viewing regions, such as the size is selected based, at least in part, on the concentration of the pharmaceutical agent and designed to minimize or reduce visual disturbances for the eye.

J2. The method of example J1, wherein the ophthalmic lenses comprise one or more features of the ophthalmic lenses of examples B1-B57.

K1. A method of managing progression of myopia in an eye, comprising: detecting (or identifying) myopia and/or progression of myopia in an eye; determining the concentration of the pharmaceutical agent to be prescribed for use to slow, retard or control the progression of myopia; and selecting an ophthalmic lenses from a series or a kit or a plurality of ophthalmic lenses based on the concentration of the pharmaceutical agent in use; wherein the ophthalmic lens is an ophthalmic lens of any of examples B1-B57.

L1. A method of supplying (or manufacturing) a series of ophthalmic lenses for managing progression of myopia in an eye, comprising: providing a series of digital lens designs (e.g., in the form of manufacturing machine code files) to remote optical laboratories for use in making the series of ophthalmic lenses; determining the concentration of the pharmaceutical agent to be prescribed for use to slow, retard or control the progression of myopia; and selecting an ophthalmic lenses from a series or a kit or a plurality of ophthalmic lenses based on the concentration of the pharmaceutical agent in use; wherein the ophthalmic lens is an ophthalmic lens of any of examples B1-B57.

It will be understood that the embodiments disclosed and defined in this specification extends to all alternative combinations of two or more of the individual features mentioned or evident from the text or drawings. All these different combinations constitute various alternative aspects of the present disclosure.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

The invention claimed is:

1. An ophthalmic lens for use in conjunction with a pharmaceutical agent for an eye with myopia, the ophthalmic lens comprising:
a base lens with a front surface and a back surface;
at least one first viewing region having a first power profile, wherein the size of the at least one first viewing region is configured based, at least in part, on the concentration of the pharmaceutical agent; and
one or more myopia control elements with a power profile different than the first power profile.

2. The ophthalmic lens of claim 1, wherein the first power profile is selected to correct or substantially correct for a refractive error of the eye.

3. The ophthalmic lens of claim 1, wherein the size of at least one of the first viewing regions is selected based, at least in part, on the concentration of the pharmaceutical agent to reduce or minimize vision disturbances that may result from the change in pupillary diameter attributable to the pharmaceutical agent.

4. The ophthalmic lens of claim 1, wherein the power profile of at least one of the first viewing regions is selected based, at least in part, on the concentration of the pharmaceutical agent to reduce one or more of a third order aberration, fourth order aberration, fifth order aberration, sixth order aberration, one or more of other higher order aberrations or a combination of one or more thereof to minimize vision disturbances that may result from the change in pupillary diameter attributable to the pharmaceutical agent.

5. The ophthalmic lens of claim 1, wherein the at least one first viewing region is substantially aligned with one or more of the axes of the eye.

6. The ophthalmic lens of claim 1, wherein the size of the at least one first viewing region is configured based on one of a 95% confidence interval, a 97% confidence interval or a 99% confidence interval, wherein a confidence interval is determined by multiplying the following equation by the corresponding percentage: One of the first viewing region size for a wearer not undergoing atropine therapy+6.924+0.6266*LN (Concentration of Atropine %/100).

7. The ophthalmic lens of claim 1, wherein the size of the at least one first viewing region is configured based on the size of the first viewing region without the use of the pharmaceutical agent and a percentage of the value estimated from the equation: 6.924+0.6266*LN (Concentration of Atropine %/100).

8. The ophthalmic lens of any of claim 1, further comprising at least one second viewing region with a second power profile different than the first power profile.

9. The ophthalmic lens of claim 8, wherein the second power profile is relatively more positive in power than the first power profile and selected based, at least in part, on the concentration of the pharmaceutical agent.

10. The ophthalmic lens of claim 8, wherein the size of the at least one second viewing region is selected based, at least in part, on the concentration of the pharmaceutical agent.

11. The ophthalmic lens of claim 8, wherein the at least one second viewing region is positioned at any combination of one or more of inferior, superior, temporal, nasal, oblique, concentric co-axial, concentric non co-axial, eccentric, non-concentric, inferonasal, inferotemporal or any other position relative to the at least one first viewing region.

12. The ophthalmic lens of claim 8, wherein the second power profile in the at least one second viewing region ranges from about ≥+0.50D to about ≤+3.50D or about ≥+0.25D to about ≤+4.00D or about ≥+0.25D to about ≤+5.00D.

13. The ophthalmic lens of claim 1, wherein the ophthalmic lens further comprises any combination of one or more of a light absorbing filter, a light absorbing element, a photochromic filter, a photo mask, and a phase shift mask in one or more regions of the lens and is configured based, at least in part, on the concentration of the pharmaceutical agent.

14. The ophthalmic lens of claim 1, wherein the combination of one or more of the shape, pattern, position and power profile of the one or more myopia control elements relative to the at least one first viewing region is selected based, at least in part, on the concentration of the pharmaceutical agent.

15. The ophthalmic lens of claim 1, wherein the at least one first viewing region is substantially devoid of myopia control elements.

16. The ophthalmic lens of claim 1, wherein the one or more myopia control elements are a plurality of lenslets, one or more rings, opaque elements, non-refractive elements, defocus elements, or a plurality of discrete elements and may be a variation of the power profile of the lens that provides any combination of one or more of myopic defocus, hyperopic defocus, no defocus, or an extended depth of focus.

17. The ophthalmic lens of claim 1, wherein the one or more myopia control elements are any combination of one or more of refractive, meta-surfaces, diffractive, contrast modulating, light scattering, aberrated, holographic, light diffusing, light deviating, light amplitude modulating and/or phase modulating.

18. The ophthalmic lens of claim 1, wherein the arrangement, type, size, magnitude, strength, location, and/or fill factor of the one or more myopia control elements is configured based, at least in part, on the concentration of the pharmaceutical agent.

19. The ophthalmic lens of claim 1, wherein the shape, position and/or power profile of the one or more myopia control elements relative to the at least one first viewing region is selected based, at least in part, such that a rotational asymmetry of power profile is created by the one or more myopia control elements.

20. The ophthalmic lens of claim 1, wherein the strength of the one or more myopia control elements decreases with increasing concentration of the pharmaceutical agent.

21. The ophthalmic lens of claim 1, wherein the ophthalmic lens is a spectacle lens or a contact lens.

22. The ophthalmic lens of claim 1, wherein the pharmaceutical agent is a muscarinic receptor antagonist.

23. The ophthalmic lens of claim 1, wherein the pharmaceutical agent is Atropine or Atropine related compound.

24. An ophthalmic lens series for use in conjunction with a pharmaceutical agent for an eye with myopia, the lenses in the series comprising:
a base lens with a front and back surface and one or more myopia control elements;
at least one first viewing region with a first power profile selected to correct for a refractive error of the eye and to substantially control, minimize, and/or reduce one or more of the higher order aberrations of the eye, and wherein the size of the at least one first viewing region is configured based, at least in part, on the concentration of the pharmaceutical agent.

25. The ophthalmic lens series of claim 24, wherein the ophthalmic lenses are contact lenses.

26. An ophthalmic lens series for use in conjunction with a pharmaceutical agent for an eye with myopia, the lenses of the series comprising:
a base lens with a front and back surface and one or more myopia control elements interspersed on and/or in the lens;
at least one first viewing region with a first power profile selected to substantially correct for a refractive error of the eye, wherein the size of at least one of the first viewing regions is configured based, at least in part, on the concentration of the pharmaceutical agent; and
at least one second viewing region with a second power profile that is different than the at least one first viewing region and selected based, at least in part, on the concentration of the pharmaceutical agent and the different power ranges from about ≥+0.50D to about ≤+3.50D.

27. The ophthalmic lens series of claim 26, wherein the ophthalmic lenses are contact lenses.

28. A spectacle lens series for use in conjunction with a pharmaceutical agent for an eye with myopia, the lenses in the series comprising:
a base lens with a front and back surface and one or more myopia control elements interspersed on and/or in the lens;
at least one first viewing region with a first power profile selected to substantially correct for a refractive error of the eye, wherein the size of at least one first viewing region is configured based, at least in part, on the concentration of the pharmaceutical agent;
at least one second viewing region with a second power profile that is relatively more positive than the at least one first viewing region from about ≥+0.50D to about ≤+3.50D, and selected based, at least in part, on the concentration of the pharmaceutical agent in use, and positioned at any combination of one or more of central, peripheral, inferior, superior, temporal, nasal, oblique, concentric co-axial, concentric non co-axial, eccentric, non-concentric, inferonasal, inferotemporal or any other position relative to the at least one first viewing region.

29. The spectacle lens series of claim 28, wherein the lenses in the series further comprise a light absorbing filter or a light absorbing element or a photochromic filter or a photo mask or a phase shift mask in one or more regions of the lens and is configured based, at least in part, on the concentration of the pharmaceutical agent.

30. The ophthalmic lens series of claim 28, wherein the pharmaceutical agent is Atropine or Atropine related compound.

* * * * *